United States Patent
Errico et al.

(10) Patent No.: US 7,747,324 B2
(45) Date of Patent: *Jun. 29, 2010

(54) ELECTRICAL STIMULATION TREATMENT OF BRONCHIAL CONSTRICTION

(75) Inventors: Joseph P. Errico, Green Brook, NJ (US); James R. Pastena, Succasunna, NJ (US); Steven Mendez, Chester, NJ (US); Hecheng Hu, Cedar Grove, NJ (US); Arthur Ross, Mendham, NJ (US)

(73) Assignee: ElectroCore LLC, Morris Plains, NJ (US)

( * ) Notice: Subject to any disclaimer, the term of this patent is extended or adjusted under 35 U.S.C. 154(b) by 672 days.

This patent is subject to a terminal disclaimer.

(21) Appl. No.: 11/591,340

(22) Filed: Nov. 1, 2006

(65) Prior Publication Data

US 2007/0106339 A1 May 10, 2007
US 2010/0042178 A9 Feb. 18, 2010

Related U.S. Application Data

(60) Provisional application No. 60/736,001, filed on Nov. 10, 2005, provisional application No. 60/772,361, filed on Feb. 10, 2006, provisional application No. 60/814,313, filed on Jun. 16, 2006, provisional application No. 60/786,564, filed on Mar. 28, 2006, provisional application No. 60/736,002, filed on Nov. 10, 2005.

(51) Int. Cl.
*A61N 1/36* (2006.01)
(52) U.S. Cl. .................................................. 607/42
(58) Field of Classification Search .............. 607/42
See application file for complete search history.

(56) References Cited

U.S. PATENT DOCUMENTS

| | | | |
|---|---|---|---|
| 3,946,745 A | 3/1976 | Hsiang-Lai et al. |
| 3,949,743 A | 4/1976 | Shanbrom |
| 4,305,402 A | 12/1981 | Katims |
| 4,351,330 A | 9/1982 | Scarberry |
| 4,503,863 A | 3/1985 | Katims |
| 4,649,935 A | 3/1987 | Charmillot et al. |
| 4,765,322 A | 8/1988 | Charmillot et al. |
| 4,904,472 A | 2/1990 | Belardinelli et al. |
| 4,945,910 A | 8/1990 | Budyko et al. |
| 4,989,604 A | 2/1991 | Fang |
| 5,054,486 A | 10/1991 | Yamada |

(Continued)

FOREIGN PATENT DOCUMENTS

WO 9301862 2/1993

(Continued)

OTHER PUBLICATIONS

International search Report of International Application PCT/US2006/42823.

(Continued)

*Primary Examiner*—Kennedy J Schaetzle
*Assistant Examiner*—Jessica Sarcione
(74) *Attorney, Agent, or Firm*—John T. Raffle

(57) ABSTRACT

Methods and devices for treating bronchial constriction related to asthma and anaphylaxis wherein the treatment includes providing an electrical impulse to a selected region of the vagus nerve and/or the lungs of a patient suffering from bronchial constriction.

13 Claims, 15 Drawing Sheets

U.S. PATENT DOCUMENTS

| | | |
|---|---|---|
| 5,107,835 A | 4/1992 | Thomas |
| 5,109,846 A | 5/1992 | Thomas |
| 5,123,413 A | 6/1992 | Hasegawa et al. |
| 5,135,480 A | 8/1992 | Bannon et al. |
| 5,152,286 A | 10/1992 | Sitko et al. |
| 5,405,362 A | 4/1995 | Kramer et al. |
| 5,405,366 A | 4/1995 | Fox et al. |
| 5,437,291 A | 8/1995 | Pasricha et al. |
| 5,454,840 A | 10/1995 | Krakovsky et al. |
| 5,540,730 A | 7/1996 | Terry, Jr. et al. |
| 5,620,463 A | 4/1997 | Drolet |
| 5,658,322 A | 8/1997 | Fleming |
| 5,674,205 A | 10/1997 | Pasricha et al. |
| 5,690,692 A | 11/1997 | Fleming |
| 5,707,400 A | 1/1998 | Terry, Jr. et al. |
| 5,814,078 A | 9/1998 | Zhou et al. |
| 5,849,026 A | 12/1998 | Zhou et al. |
| 5,891,182 A | 4/1999 | Fleming |
| 5,911,218 A | 6/1999 | DiMarco |
| 5,931,806 A | 8/1999 | Shimada |
| 5,956,501 A | 9/1999 | Brown |
| 5,972,026 A | 10/1999 | Laufer et al. |
| 5,995,873 A | 11/1999 | Rhodes |
| 6,006,134 A | 12/1999 | Hill et al. |
| 6,043,273 A | 3/2000 | Duhaylongsod |
| 6,060,454 A | 5/2000 | Duhaylongsod |
| 6,083,249 A | 7/2000 | Familoni |
| 6,083,255 A | 7/2000 | Laufer et al. |
| 6,087,394 A | 7/2000 | Duhaylongsod |
| 6,101,412 A | 8/2000 | Duhaylongsod |
| 6,125,301 A | 9/2000 | Capel |
| 6,127,410 A | 10/2000 | Duhaylongsod |
| 6,141,589 A | 10/2000 | Duhaylongsod |
| 6,198,970 B1 | 3/2001 | Freed et al. |
| 6,200,333 B1 | 3/2001 | Laufer |
| 6,203,562 B1 | 3/2001 | Ohkubo |
| 6,212,432 B1 | 4/2001 | Matsuura |
| 6,230,052 B1 | 5/2001 | Wolff et al. |
| 6,258,087 B1 | 7/2001 | Edwards et al. |
| 6,273,886 B1 | 8/2001 | Edwards et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,325,798 B1 | 12/2001 | Edwards et al. |
| 6,327,503 B1 | 12/2001 | Familoni |
| 6,341,236 B1 | 1/2002 | Osorio et al. |
| 6,342,221 B1 | 1/2002 | Thorpe et al. |
| 6,356,786 B1 | 3/2002 | Rezai et al. |
| 6,356,787 B1 | 3/2002 | Rezai et al. |
| 6,363,937 B1 | 4/2002 | Hovda et al. |
| 6,366,814 B1 | 4/2002 | Boveja et al. |
| 6,402,744 B2 | 6/2002 | Edwards et al. |
| 6,411,852 B1 | 6/2002 | Danek et al. |
| 6,414,018 B1 | 7/2002 | Duhaylongsod |
| 6,423,058 B1 | 7/2002 | Edwards et al. |
| 6,424,864 B1 | 7/2002 | Matsuura |
| 6,438,423 B1 | 8/2002 | Rezai et al. |
| 6,440,128 B1 | 8/2002 | Edwards et al. |
| 6,464,697 B1 | 10/2002 | Edwards et al. |
| 6,485,416 B1 | 11/2002 | Platt et al. |
| 6,547,776 B1 | 4/2003 | Gaiser et al. |
| 6,549,808 B1 | 4/2003 | Gisel et al. |
| 6,562,034 B2 | 5/2003 | Edwards et al. |
| 6,587,719 B1 | 7/2003 | Barrett et al. |
| 6,609,030 B1 | 8/2003 | Rezai et al. |
| 6,610,713 B2 | 8/2003 | Tracey |
| 6,629,951 B2 | 10/2003 | Laufer et al. |
| 6,633,779 B1 | 10/2003 | Schuler et al. |
| 6,656,960 B2 | 12/2003 | Puskas |
| 6,675,047 B1 | 1/2004 | Konoplev et al. |
| 6,676,686 B2 | 1/2004 | Naganuma |
| 6,681,136 B2 | 1/2004 | Schuler et al. |
| 6,711,436 B1 | 3/2004 | Duhaylongsod |
| 6,712,074 B2 | 3/2004 | Edwards et al. |
| 6,738,667 B2 | 5/2004 | Deno et al. |
| 6,752,765 B1 | 6/2004 | Jensen et al. |
| 6,755,849 B1 | 6/2004 | Gowda et al. |
| 6,778,854 B2 | 8/2004 | Puskas |
| 6,819,956 B2 | 11/2004 | DiLorenzo |
| 6,838,429 B2 | 1/2005 | Paslin |
| 6,853,862 B1 | 2/2005 | Marchal et al. |
| 6,871,092 B2 | 3/2005 | Piccone |
| 6,871,099 B1 | 3/2005 | Whitehurst et al. |
| 6,872,206 B2 | 3/2005 | Edwards et al. |
| 6,885,888 B2 | 4/2005 | Rezai |
| 6,913,616 B2 | 7/2005 | Hamilton et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,957,106 B2 | 10/2005 | Schuler et al. |
| 6,961,622 B2 | 11/2005 | Gilbert |
| 6,970,742 B2 | 11/2005 | Mann et al. |
| 6,974,224 B2 | 12/2005 | Thomas-Benedict |
| 7,142,910 B2 | 11/2006 | Puskas |
| 7,292,890 B2 | 11/2007 | Whitehurst et al. |
| 7,310,552 B2 | 12/2007 | Puskas |
| 2002/0002387 A1 | 1/2002 | Naganuma |
| 2002/0010495 A1 | 1/2002 | Freed et al. |
| 2002/0016344 A1 | 2/2002 | Tracey |
| 2002/0072738 A1 | 6/2002 | Edwards et al. |
| 2002/0091379 A1 | 7/2002 | Danek et al. |
| 2002/0107515 A1 | 8/2002 | Edwards et al. |
| 2002/0111386 A1 | 8/2002 | Sekins et al. |
| 2002/0116030 A1 | 8/2002 | Rezai |
| 2002/0143373 A1 | 10/2002 | Courtnage et al. |
| 2002/0151888 A1 | 10/2002 | Edwards et al. |
| 2002/0183682 A1 | 12/2002 | Darvish et al. |
| 2002/0198570 A1 | 12/2002 | Puskas |
| 2002/0198574 A1 | 12/2002 | Gumpert |
| 2003/0023287 A1 | 1/2003 | Edwards et al. |
| 2003/0074039 A1 | 4/2003 | Puskas |
| 2003/0093128 A1 | 5/2003 | Freed et al. |
| 2003/0144572 A1 | 7/2003 | Oschman et al. |
| 2003/0181949 A1 | 9/2003 | Whale |
| 2003/0216791 A1 | 11/2003 | Schuler et al. |
| 2003/0216792 A1 | 11/2003 | Levin et al. |
| 2003/0233099 A1* | 12/2003 | Danaek et al. .............. 606/96 |
| 2004/0010289 A1 | 1/2004 | Biggs et al. |
| 2004/0029849 A1 | 2/2004 | Schatzberg et al. |
| 2004/0030368 A1 | 2/2004 | Kemeny et al. |
| 2004/0044390 A1 | 3/2004 | Szeles |
| 2004/0059383 A1 | 3/2004 | Puskas |
| 2004/0073278 A1 | 4/2004 | Pachys |
| 2004/0088030 A1 | 5/2004 | Jung, Jr. |
| 2004/0088036 A1 | 5/2004 | Gilbert |
| 2004/0106954 A1 | 6/2004 | Whitehurst et al. |
| 2004/0116981 A1 | 6/2004 | Mazar |
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127953 A1* | 7/2004 | Kilgore et al. .............. 607/46 |
| 2004/0127958 A1 | 7/2004 | Mazar et al. |
| 2004/0147969 A1 | 7/2004 | Mann et al. |
| 2004/0147988 A1 | 7/2004 | Stephens |
| 2004/0162597 A1 | 8/2004 | Hamilton et al. |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0176803 A1 | 9/2004 | Whelan et al. |
| 2004/0176805 A1 | 9/2004 | Whelan et al. |
| 2004/0204747 A1 | 10/2004 | Kemeny et al. |
| 2004/0215289 A1 | 10/2004 | Fukui |

| | | | | | | |
|---|---|---|---|---|---|---|
| 2004/0220621 A1 | 11/2004 | Zhou et al. | | 2005/0267536 A1 | 12/2005 | Freeman et al. |
| 2004/0230251 A1 | 11/2004 | Schuler et al. | | 2005/0277993 A1 | 12/2005 | Mower |
| 2004/0230252 A1 | 11/2004 | Kullok et al. | | 2005/0283197 A1 | 12/2005 | Daum et al. |
| 2004/0243182 A1 | 12/2004 | Cohen et al. | | 2006/0100666 A1 | 5/2006 | Wilkinson |
| 2004/0249416 A1 | 12/2004 | Yun et al. | | 2006/0135998 A1 | 6/2006 | Libbus et al. |
| 2005/0004609 A1 | 1/2005 | Stahmann et al. | | 2006/0167498 A1 | 7/2006 | DiLorenzo |
| 2005/0004631 A1 | 1/2005 | Benedict | | 2006/0178703 A1 | 8/2006 | Huston |
| 2005/0010263 A1 | 1/2005 | Schauerte | | 2006/0247683 A1 | 11/2006 | Danek |
| 2005/0010270 A1 | 1/2005 | Laufer | | 2006/0259028 A1 | 11/2006 | Utley |
| 2005/0015117 A1 | 1/2005 | Gerber | | 2006/0259029 A1 | 11/2006 | Utley |
| 2005/0021092 A1 | 1/2005 | Yun et al. | | 2006/0259030 A1 | 11/2006 | Utley |
| 2005/0059153 A1 | 3/2005 | George et al. | | 2006/0287679 A1 | 12/2006 | Stone |
| 2005/0065553 A1 | 3/2005 | Ezra et al. | | 2007/0027496 A1 | 2/2007 | Parnis et al. |
| 2005/0065562 A1 | 3/2005 | Rezai | | 2007/0060954 A1 | 3/2007 | Cameron |
| 2005/0065567 A1 | 3/2005 | Lee et al. | | 2007/0106337 A1 | 5/2007 | Errico |
| 2005/0065573 A1 | 3/2005 | Rezai | | 2007/0106338 A1 | 5/2007 | Errico |
| 2005/0065574 A1 | 3/2005 | Rezai | | 2007/0106339 A1 | 5/2007 | Errico et al. |
| 2005/0075701 A1 | 4/2005 | Shafer | | 2007/0191902 A1 | 8/2007 | Errico et al. |
| 2005/0075702 A1 | 4/2005 | Shafer | | 2007/0225768 A1 | 9/2007 | Dobak et al. |
| 2005/0076909 A1 | 4/2005 | Stahmann et al. | | 2008/0183248 A1 | 7/2008 | Rezai et al. |
| 2005/0080461 A1 | 4/2005 | Stahmann et al. | | | | |
| 2005/0090722 A1 | 4/2005 | Perez | | | | |
| 2005/0107829 A1 | 5/2005 | Edwards et al. | | | | |
| 2005/0125044 A1 | 6/2005 | Tracey | | | | |
| 2005/0143788 A1 | 6/2005 | Yun et al. | | | | |
| 2005/0149146 A1 | 7/2005 | Boveja et al. | | | | |
| 2005/0153885 A1 | 7/2005 | Yun et al. | | | | |
| 2005/0159736 A9 | 7/2005 | Danek et al. | | | | |
| 2005/0165456 A1 | 7/2005 | Mann et al. | | | | |
| 2005/0177192 A1 | 8/2005 | Rezai et al. | | | | |
| 2005/0182288 A1 | 8/2005 | Zabara | | | | |
| 2005/0187579 A1 | 8/2005 | Danek et al. | | | | |
| 2005/0216062 A1 | 9/2005 | Herbst | | | | |
| 2005/0222628 A1 | 10/2005 | Krakousky | | | | |
| 2005/0222635 A1 | 10/2005 | Krakovsky | | | | |
| 2005/0222651 A1 | 10/2005 | Jung | | | | |
| 2005/0228054 A1 | 10/2005 | Tatton | | | | |
| 2005/0228459 A1 | 10/2005 | Levin et al. | | | | |
| 2005/0228460 A1 | 10/2005 | Levin et al. | | | | |
| 2005/0234523 A1 | 10/2005 | Levin et al. | | | | |
| 2005/0238693 A1 | 10/2005 | Whyte | | | | |
| 2005/0240241 A1 | 10/2005 | Yun et al. | | | | |
| 2005/0245992 A1 | 11/2005 | Persen et al. | | | | |
| 2005/0251213 A1 | 11/2005 | Freeman | | | | |
| 2005/0256028 A1 | 11/2005 | Yun et al. | | | | |
| 2005/0261747 A1 | 11/2005 | Schuler et al. | | | | |

FOREIGN PATENT DOCUMENTS

| | | |
|---|---|---|
| WO | WO 01/89526 A1 | 11/2001 |
| WO | WO 2004/078252 A2 | 9/2004 |

OTHER PUBLICATIONS

International Preliminary Report On Patentability for corresponding PCT application PCT/US2006/042752, Mar. 3, 2009.

International Preliminary Report on Patentability for PCT/US2006/042823, dated Aug. 21, 2008.

International Search Report and Written Opinion for corresponding application PCT/US2006/42752.

International Search Report and Written Opinion for PCT application PCT/US2009/038081, Jun. 1, 2009.

Supplemental European Search Report for EP Application No. 06827343, Aug. 21, 2009.

Supplemental European Search Report for EP Application No. 06827386.1, Aug. 21, 2009.

U.S. Appl. No. 60/206,364, Title: Vagus Nerve Stimulation Attenuation of the Systemic Inflammatory Response to Endotoxin, Filing Date: May 23, 2000, Inventor: Tracey.

Guarini et al., "Efferent Vagal Fibre Stimulation Blunts Nuclear Factor-kB Activation and Protects Against Hypovolemic Hemorrhagic Shock", *Circulation* 2003 vol. 107 pp. 1189-1194.

* cited by examiner

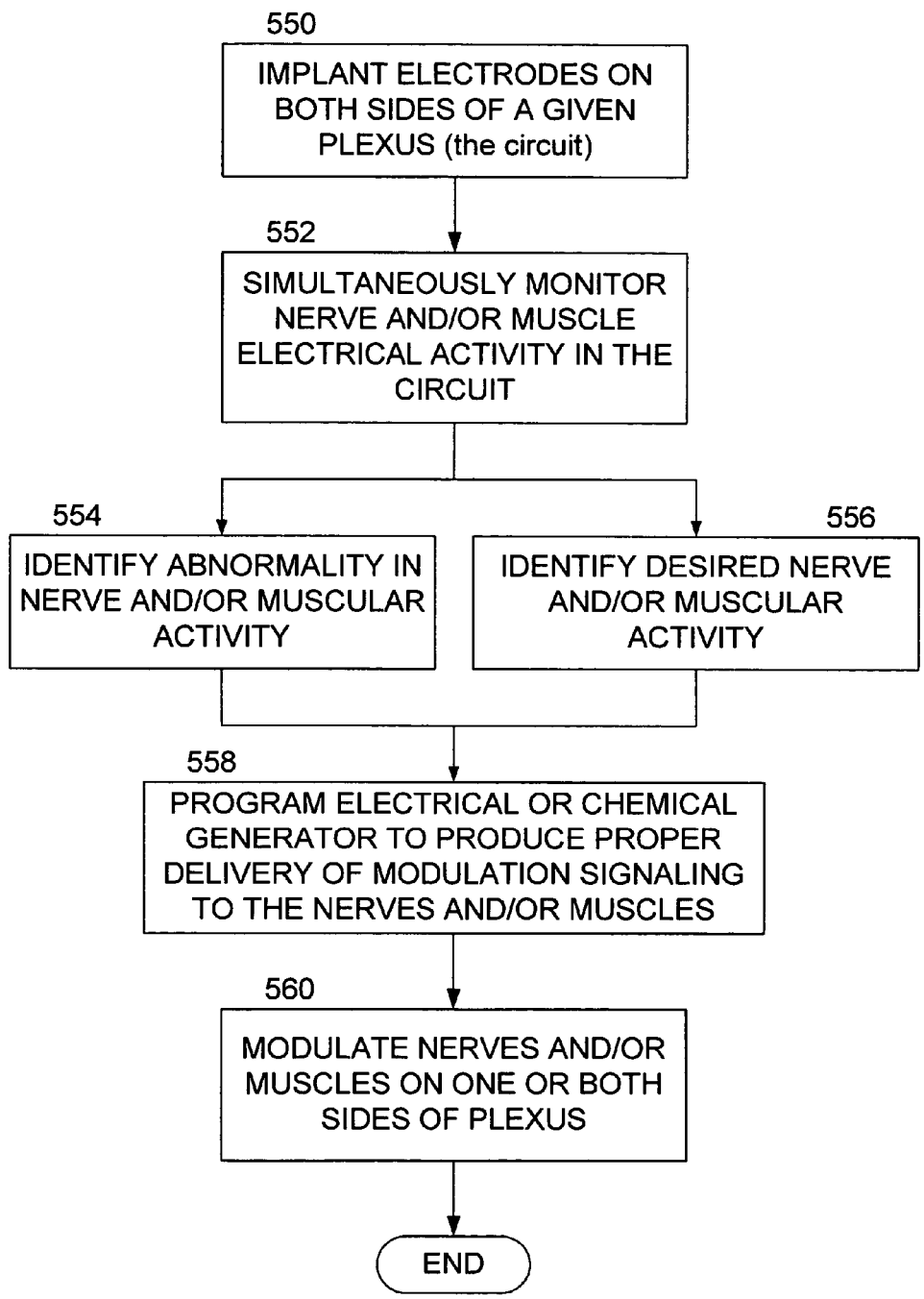

ELECTRICAL STIMULATION TREATMENT OF BRONCHIAL CONSTRICTION

CROSS REFERENCE TO RELATED APPLICATIONS

This application claims the benefit of U.S. Provisional Patent Application Nos. 60/736,001, filed Nov. 10, 2005; 60/772,361, filed Feb. 10, 2006; 60/814,313, filed Jun. 16, 2006; and 60/786,564, filed Mar. 28, 2006, the entire disclosures of which are hereby incorporated by reference. This application also claims the benefit of U.S. Provisional Patent Application No. 60/736,002, filed Nov. 10, 2005.

BACKGROUND OF THE INVENTION

The present invention relates to the field of delivery of electrical impulses (and/or fields) to bodily tissues for therapeutic purposes, and more specifically to devices and methods for treating conditions associated with bronchial constriction There are a number of treatments for various infirmities that require the destruction of otherwise healthy tissue in order to affect a beneficial effect. Malfunctioning tissue is identified, and then lesioned or otherwise compromised in order to affect a beneficial outcome, rather than attempting to repair the tissue to its normal functionality. While there are a variety of different techniques and mechanisms that have been designed to focus lesioning directly onto the target nerve tissue, collateral damage is inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant, for example, at least one popular diet pill of the late 1990's was subsequently found to cause heart attacks and strokes.

Unfortunately, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Electrical stimulation of the brain with implanted electrodes has been approved for use in the treatment of various conditions, including pain and movement disorders including essential tremor and Parkinson's disease. The principle behind these approaches involves disruption and modulation of hyperactive neuronal circuit transmission at specific sites in the brain. As compared with the very dangerous lesioning procedures in which the portions of the brain that are behaving pathologically are physically destroyed, electrical stimulation is achieved by implanting electrodes at these sites to, first sense aberrant electrical signals and then to send electrical pulses to locally disrupt the pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure requires penetrating the skull, and inserting an electrode into the brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neurovasculature.

One of the most successful modern applications of this basic understanding of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Around this time, it was also found that the electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to Deno, et al., the disclosure of which is incorporated herein by reference).

Another application of electrical stimulation of nerves has been the treatment of radiating pain in the lower extremities by means of stimulation of the sacral nerve roots at the bottom of the spinal cord (see U.S. Pat. No. 6,871,099 to Whitehurst, et al., the disclosure of which is incorporated herein by reference).

The smooth muscles that line the bronchial passages are controlled by a confluence of vagus and sympathetic nerve fiber plexuses. Spasms of the bronchi during asthma attacks and anaphylactic shock can often be directly related to pathological signaling within these plexuses. Anaphylactic shock and asthma are major health concerns.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release of the molecules that mediate the inflammatory process. The second strategy is to provide a smooth muscle relaxant (an anticholinergic and/or anti-adrenergic medication) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Anaphylaxis likely ranks among the other airway occluding disorders of this type as the most deadly, claiming more than eight thousand deaths per year in the United States alone. Anaphylaxis (the most severe from of which is anaphylactic shock) is a severe and rapid systemic allergic reaction to an allergen. Minute amounts of allergens may cause a life-threatening anaphylactic reaction. Anaphylaxis may occur after ingestion, inhalation, skin contact or injection of an allergen. Anaphylactic shock usually results in death in minutes if untreated. Anaphylactic shock is a life-threatening medical emergency because of rapid constriction of the airway. Brain damage sets in quickly without oxygen. Anaphylactic shock itself accounts for approximately 1,500 deaths every year in the United States.

The triggers for these fatal reactions range from foods (nuts and shellfish), to insect stings (bees), to medication (radiocontrasts and antibiotics). It is estimated 1.3 to 13 million people in the United States are allergic to venom associated with insect bites; 27 million are allergic to antibiotics; and 5-8 million suffer food allergies. All of these individuals are at risk of anaphylactic shock from exposure to any of the foregoing allergens. In addition, anaphylactic shock can be brought on by exercise. Yet all are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

Anaphylactic shock requires advanced medical care immediately. Current emergency measures include rescue breathing; administration of epinephrine; and/or intubation if possible. Rescue breathing may be hindered by the closing airway but can help if the victim stops breathing on his own. Clinical treatment typically consists of antihistamines (which inhibit the effects of histamine at histamine receptors) which are usually not sufficient in anaphylaxis, and high doses of intravenous corticosteroids. Hypotension is treated with intravenous fluids and sometimes vasoconstrictor drugs. For bronchospasm, bronchodilator drugs such as salbutamol are employed.

Given the common mediators of both asthmatic and anaphylactic bronchoconstriction, it is not surprising that asthma sufferers are at a particular risk for anaphylaxis. Still, estimates place the numbers of people who are susceptible to such responses at more than 40 million in the United States alone.

Tragically, many of these patients are fully aware of the severity of their condition, and die while struggling in vain to manage the attack medically. Many of these incidents occur in hospitals or in ambulances, in the presence of highly trained medical personnel who are powerless to break the cycle of inflammation and bronchoconstriction (and life-threatening hypotension in the case of anaphylaxis) affecting their patient.

Unfortunately, prompt medical attention for anaphylactic shock and asthma are not always available. For example, epinephrine is not always available for immediate injection. Even in cases where medication and attention is available, life saving measures are often frustrated because of the nature of the symptoms. Constriction of the airways frustrates resuscitation efforts, and intubation may be impossible because of swelling of tissues.

Typically, the severity and rapid onset of anaphylactic reactions does not render the pathology amenable to chronic treatment, but requires more immediately acting medications. Among the most popular medications for treating anaphylaxis is epinephrine, commonly marketed in so-called "Epipen" formulations and administering devices, which potential sufferers carry with them at all times. In addition to serving as an extreme bronchodilator, epinephrine raises the patient's heart rate dramatically in order to offset the hypotension that accompanies many reactions. This cardiovascular stress can result in tachycardia, heart attacks and strokes.

Unlike cardiac arrhythmias, which can be treated chronically with pacemaker technology, or in emergent situations with equipment like defibrillators (implantable and external), there is virtually no commercially available medical equipment that can chronically reduce the baseline sensitivity of the muscle tissue in the airways to reduce the predisposition to asthma attacks, or to break the cycle of bronchial constriction associated with an acute asthma attack or anaphylaxis.

Accordingly, there is a need in the art for new products and methods for treating the immediate symptoms of anaphylactic shock and asthma.

SUMMARY OF THE INVENTION

The present invention involves products and methods of treatment of asthma, anaphylaxis, and other pathologies involving the constriction of the primary airways, utilizing an electrical signal that may be applied to the vagus nerve to temporarily block and/or modulate the signals in the vagus nerve.

In a first embodiment, the present invention contemplates an electrical impulse delivery device that delivers one or more electrical impulses to at least one selected region of the vagus nerve to block and/or modulate signals to the muscle fibers surrounding the bronchi, and/or block and/or affect histamine response of the vagus nerve, facilitating opening of airways.

In another embodiment, methods in accordance with the present invention contemplate delivery of one or more electrical impulses to at least one selected region of the vagus nerve to block and/or modulate signals to the muscle fibers surrounding the bronchi, and/or block and/or affect histamine response of the vagus nerve, facilitating opening of airways.

It shall be understood that the activation of such impulses may be directed manually by a patient suffering from bronchospasm, depending on the embodiment.

In one or more embodiments, the impulses are applied in a manner that blocks and/or affects the constriction of the smooth muscle lining the bronchial passages to relieve the spasms that occur during anaphylactic shock or asthma attacks. The impulses may be applied by positioning leads on the nerves that control bronchial activity such as the anterior and posterior bronchial branches of the right and left branches of the vagus nerve, which join with fibers from the sympathetic nerve chain to form the anterior and posterior pulmonary plexuses. Leads may be positioned above both the pulmonary and cardiac branches of the vagus nerve to include a stimulus and/or blocking and/or modulation of both organs. It shall also be understood that leadless impulses as shown in the art may also be utilized for applying impulses to the target regions.

The mechanisms by which the appropriate impulse is applied to the selected region of the vagus nerve can include positioning the distal ends of an electrical lead or leads in the vicinity of the nervous tissue controlling the pulmonary and/or cardiac muscles, which leads are coupled to an implantable or external electrical impulse generating device. The electric field generated at the distal tip of the lead creates a field of effect that permeates the target nerve fibers and causes the blocking and/or modulation of signals to the subject muscles, and/or the blocking and/or affecting of histamine response.

The application of electrical impulses, either to the vagus nerve or the fibers branching off the vagus nerve to the bronchial muscles to modulate the parasympathetic tone in order to relax the smooth muscle or block and/or affect the constriction of the bronchial passageways to reduce airway constriction during pathological inflammatory responses that are associated with asthma and anaphylaxis, is more completely described in the following detailed description of the invention, with reference to the drawings provided herewith, and in claims appended hereto.

The inventors submit that the cause of many physiological disorders may be a dysfunction in any one nerve, or a combination of nerves and/or nerve clusters (ganglia and/or plexuses), and that the proper treatment of such a dysfunction by electrical stimulation cannot be effective without a method that takes these alternative pathologies into consideration. More particularly, with respect to organ function, including but not limited to the respiratory, cardiovascular, digestive, reproductive, and renal-urinary systems, the nerves most directly involved with motor and sensory control are those of the tenth cranial nerve (the vagus nerve) and the sympathetic nerves. It shall be understood that the sympathetic nerve fibers emanating from the chain that extends along the anterior outside of the vertebral column, in conjunction with the fibers of the spinal cord nerve roots that join with the sympathetic fibers, form the sympathetic nervous system. The plexuses and ganglia, such as the celiac, pulmonary, cardiac, hepatic, mesenteric plexuses, that control the organ function are formed, from one side by, the afferent and efferent fibers of the vagus nerve (or in limited instances by others of the cranial nerves) and on the other side by the fibers of the sympathetic nervous system. The present invention has applicability in treating disorders that benefit from simultaneous monitoring and/or modulation of one or more sympathetic nerves, or one or more cranial nerves, or the plexus formed by the interaction of the two.

Specifically, the treatment regiments contemplated by the inventors of the present invention include the holistic monitoring of at least two of (i) the sympathetic nerve fibers (at a location distal to the sympathetic chain such that the spinal cord nerve root fibers are incorporated into the fiber bundle), (ii) the fibers of the cranial nerve branch responsible for communication with the organ or target tissue, (iii) the plexus wherein these two nerve fibers communicate, (iv) the muscles surrounding or interfacing with the pathologically responding tissue, and (v) any physical state of being that may be associated with the condition, and thusly creating a stimulation signal pattern based upon the evaluation of the monitoring such that the desired therapeutic effect results.

More specifically, the inventors hereof have made the realization that the control of the organ and/or tissue is the result of a circuit that begins in the brain, and may include at least three separate descending components, i.e., the cranial nerve, the sympathetic nerve fibers, and the spinal cord nerve roots. This circuit is, in fact, an electrical circuit, and most importantly it is being disclosed herein that it is most effective, when attempting to modify the behavior of a component in an electrical circuit, to determine the nature and function of as many of (and preferably all of) the components of the circuit before simply driving a signal into the system. This requires monitoring the appropriate components and accurately analyzing the results of that monitoring.

Physiological disorders that may be treated by this monitoring of the entire circuit, and then applying the corrective signal to the appropriate component of the system, include, but are not limited to intestinal motility disorders, sexual dysfunction, bronchial disorder (such as asthma), dysfunction of the liver, pancreatic disorders, and heart disorders, pulmonary disorders, gastrointestinal disorders, and renal and urinary complaints. The number of disorders to be treated is limited only by the number, variety, and placement of electrodes (or combinations of multiple electrodes) along the sympathetic nervous system and cranial nervous system.

In general, an allergic response is an increasing cause of adult-onset asthma cases. The allergic process, called atopy, and its connection to asthma, involves various airborne allergens or other triggers that set off a cascade of events in the immune system leading to inflammation and hyperreactivity in the airways. One description of the allergic process is as follows: The primary contributor to allergies and asthma appears to be a category of white blood cells known as helper T-cells, in particular a subgroup called TH2-cells. TH2-cells overproduce interleukins (ILs), immune factors that are molecular members of a family called cytokines, powerful agents of the inflammatory process.

Interleukins 4, 9, and 13, for example, may be responsible for a first-phase asthma attack. These interleukins stimulate the production and release of antibody groups known as immunoglobulin E (IgE). People with both asthma and allergies appear to have a genetic predisposition for overproducing IgE. During an allergic attack, these IgE antibodies can bind to special cells in the immune system called mast cells, which are generally concentrated in the lungs, skin, and mucous membranes. This bond triggers the release of a number of active chemicals, importantly potent molecules known as leukotrienes. These chemicals cause airway spasms, overproduce mucus, and activate nerve endings in the airway lining.

Another cytokine, interleukin 5, appears to contribute to a late-phase inflammatory response. This interleukin attracts white blood cells known as eosinophils. These cells accumulate and remain in the airways after the first attack. They persist for weeks and mediate the release of other damaging particles that remain in the airways.

Over the course of years the repetition of the inflammatory events involved in asthma can cause irreversible structural and functional changes in the airways, a process called remodeling. The remodeled airways are persistently narrow and can cause chronic asthma.

In accordance with one or more embodiments of the present invention, a method of treating bronchial constriction includes inducing at least one of an electric field and electromagnetic field in one or more lungs of a mammal such that one or more mitogenic factors, and that contribute to bronchial constriction are down-regulated. The mitogenic factor may include vascular endothelial growth factor (VEGF). Additionally or alternatively, the mitogenic factor may effect the production of T-helper type 2 cells (TH2).

Additionally or alternatively, the mitogenic factor may include one or more enzymes, such as one or more matrix metalloproteinases (MMPs). The one or more MMPs may include one or more of: Stromelysin-1, gelatinase A, fibroblast collagenase (MMP-1), neutrophil collagenase (MMP-8), gelatinase B (MMP-9), stromelysin-2 (MMP-10), stromelysin-3 (MMP-11), matrilysin (MMP-7), collagenase 3 (MMP-13), and TNF-alpha converting enzyme (TACE).

One or more embodiments may include inducing the field(s) by applying at least one electrical impulse to one or more field emitters. The one or more field emitters may be disposed percutaneously and/or subcutaneously to direct the field(s) toward the lung(s). For example, the one or more field emitters may be disposed at least one of on a chest of the mammal and on the back of the mammal. The one or more field emitters may include at least one of capacitive coupling electrodes and inductive coils.

One or more embodiments may include applying drive signals to the one or more field emitters to produce the at least one impulse and induce the field(s). The drive signals may include at least one of sine waves, square waves, triangle waves, exponential waves, and complex impulses. For example, the drive signals include a frequency of between about 10 Hz to 100 KHz, a duty cycle of between about 1 to 100%, and/or an amplitude of between about 1 mv/cm to about 50 mv/cm. The field(s) may be applied for a predetermined period of time, for example, between about 0.5 to about 24 hours.

Preferably, a response of the mammal to the field(s) is measured (e.g., airway pressure and/or lung volume), such that data collection and/or field adjustments may be made.

Ultimately, the inventors hereof recognize that the treatment of disorders having common symptoms may have entirely different causes, and as such must be distinguished from one another if an effective treatment is to be developed. Nowhere is this principle truer than in the potential treatment of ailments through stimulation of the nerves that control the peripheral organs and/or tissues.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 23 is a process flow diagram illustrating process steps that may be carried out for the treatment of disorders using neuromuscular modulation in accordance with one or more embodiments of the present invention.

DETAILED DESCRIPTION OF THE PREFERRED EMBODIMENTS

It shall be understood that the embodiments disclosed herein are representative of preferred aspects of the invention and are so provided as examples of the invention. The scope of the invention, however, shall not be limited to the disclosures provided herein, nor by the provisional claims appended hereto.

Treatment Approach 1

While the exact physiological causes of asthma and anaphylaxis have not been determined, the present invention postulates that the direct mediation of the smooth muscle constriction is the result of over-activity in the vagus nerve, which is a response to the flood of pro-inflammatory mediators' interacting with the receptors on the nerve fibers themselves.

It has been observed in the literature that the nervous system maintains a balance of the signals carried by the sympathetic and parasympathetic nerves. The vagus nerve, as the source of the signal to constrict bronchial smooth muscle, is thought to provide a baseline level of tonicity in the smooth muscles surrounding the bronchial passages, in order to prevent the tissue lining the airways from collapsing shut.

Specifically, one or more embodiments of the present invention consider the signals carried by the vagus (parasympathetic) nerve to cause a constriction of the smooth muscle surrounding the bronchial passages. The sympathetic nerve fibers carry the opposing signals that tend to open the bronchial passages. It should be recognized that the signals of the vagus nerve mediate a response similar to that of histamine, while the sympathetic signals generate an effect similar to epinephrine. Given the postulated balance between the parasympathetic and sympathetic signals, removing the parasympathetic signal should create an imbalance emphasizing the sympathetic signal. Along these lines, scientific literature also indicates that severing the vagus nerve in dogs will open the bronchial passages, much the same way that epinephrine does.

Figure 1:
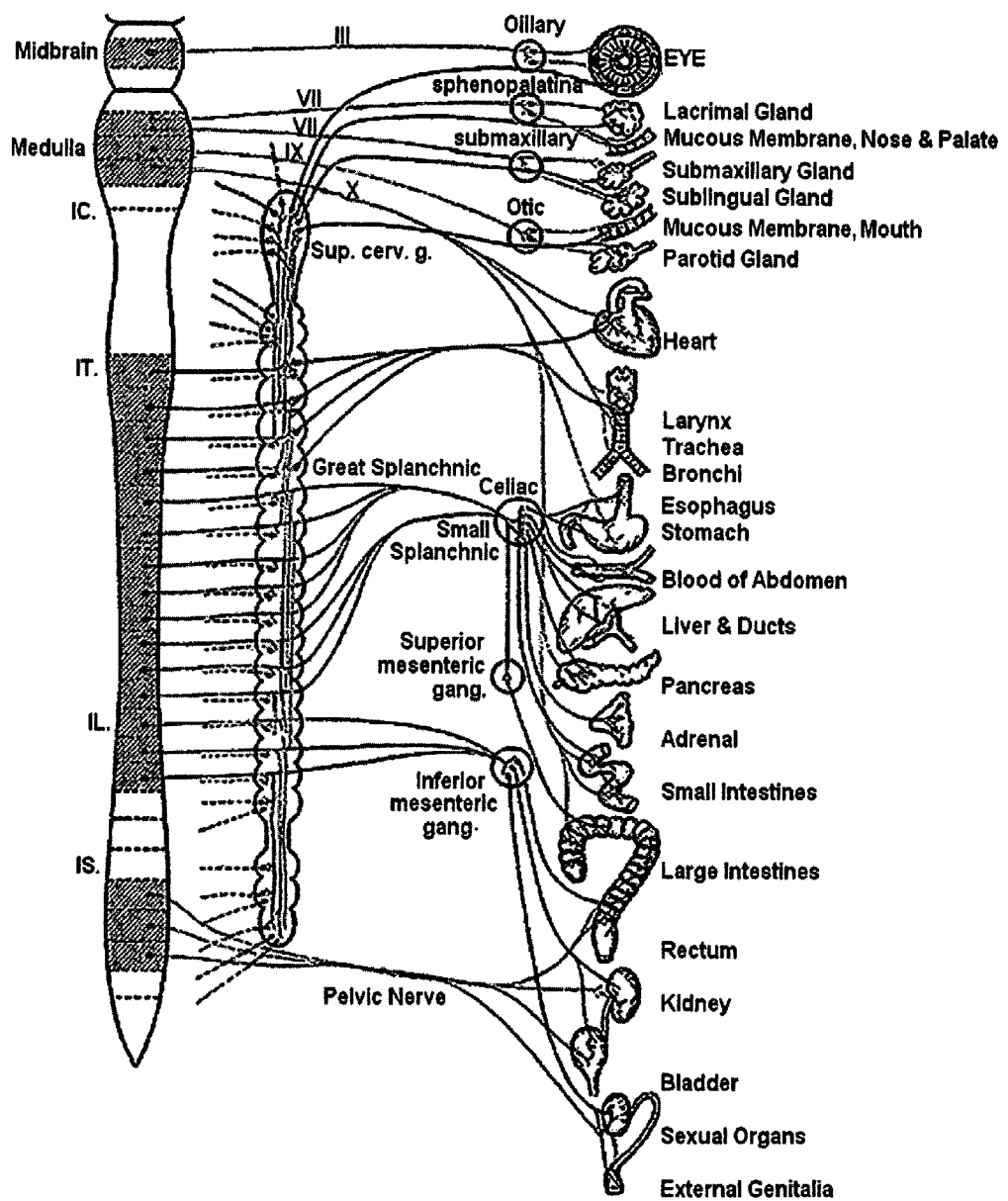
FIG. 1 is a diagrammatic view of the sympathetic and parasympathetic nerve systems.
Figure 2:
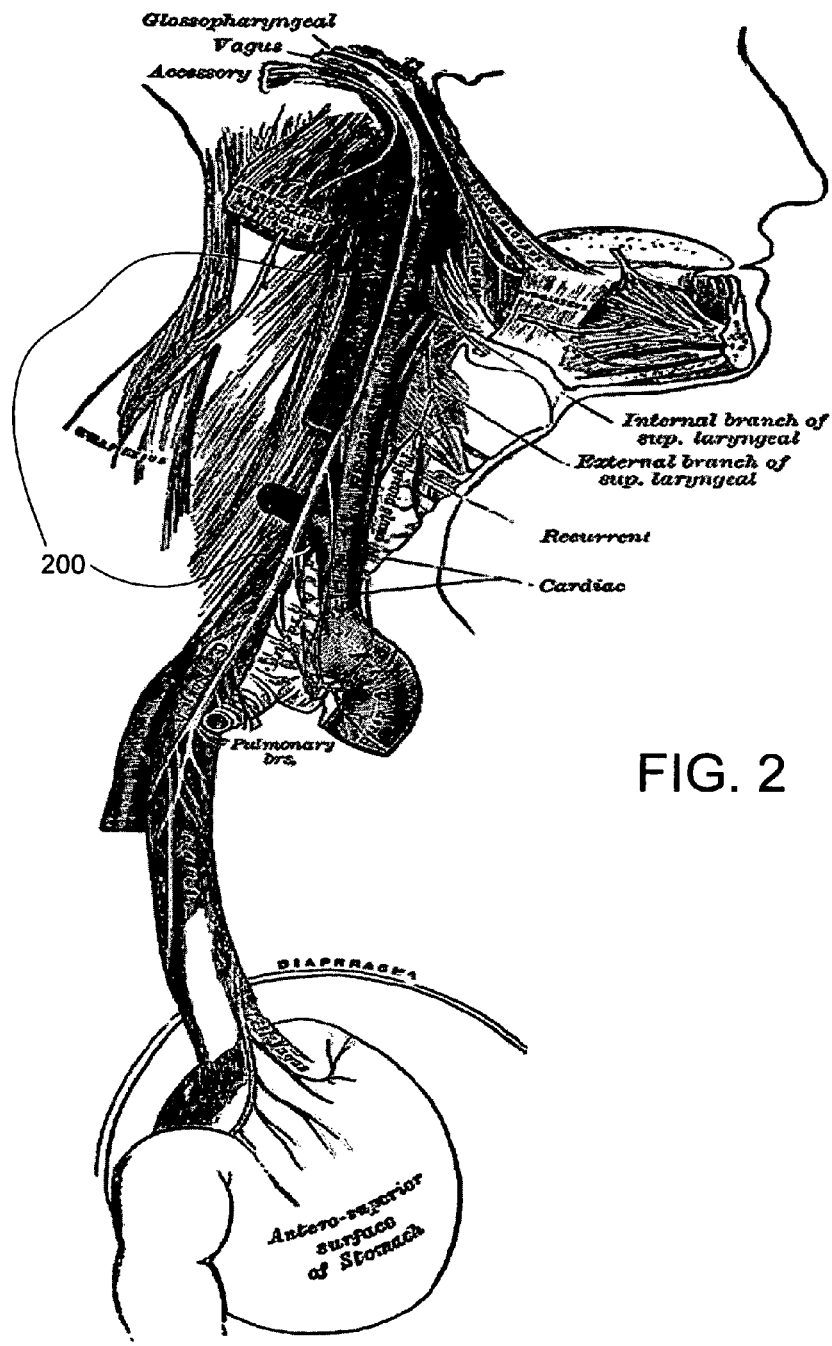
FIG. 2 is a cross-sectional anatomical illustration of selected portions of a neck, thoracic and abdominal region.

Now referring to FIGS. 1 and 2, the vagus nerve is shown in more detail. The vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguus and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, vocalization and contraction of the facial muscles in relation to emotional states. Generally speaking, this portion of the vagus nerve regulates parasympathetic tone. The VVC inhibition is released (turned off) in states of alertness. This in turn causes cardiac vagal tone to decrease and airways to open, to support responses to environmental challenges.

The parasympathetic tone is balanced in part by sympathetic innervation, which generally speaking supplies signals tending to relax the bronchial muscles so overconstriction does not occur. Overall, airway smooth muscle tone is dependent on several factors, including parasympathetic input, inhibitory influence of circulating epinephrine, NANC inhibitory nerves and sympathetic innervation of the parasympathetic ganglia. Stimulation of the vagus nerve (upregulation of tone), such as occurs in asthma attacks or anaphylactic shock, results in airway constriction and a decrease in heart rate. In general, the pathology of both severe asthma and anaphylaxis appear to be mediated by inflammatory cytokines that overwhelm receptors on the nerve cells and cause the cells to massively upregulate the parasympathetic tone.

In the case of asthma, it appears that the airway tissue has both (i) a hypersensitivity to the allergen that causes the overproduction of the cytokines that stimulate the cholenergic receptors of the nerves and/or (ii) a baseline high parasympathetic tone or a high ramp up to a strong parasympathetic tone when confronted with any level of cholenergic cytokine. The combination can be lethal. Anaphylaxis appears to be mediated predominantly by the hypersensitivity to an allergen causing the massive overproduction of cholenergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. As mentioned above, experience has shown that severing the vagus nerve (an extreme version of reducing the parasympathetic tone) has an effect similar to that of epinephrine and adrenaline on heart rate and bronchial diameter in that the heart begins to race (tachycardia) and the bronchial passageways dilate.

In accordance with at least one aspect of the present invention, the delivery, in a patient suffering from severe asthma or anaphylactic shock, of an electrical impulse sufficient to block and/or modulate transmission of signals will result in relaxation of the bronchi smooth muscle, dilating airways and/or counteract the effect of histamine on the vagus nerve. Depending on the placement of the impulse, the signal blocking and/or modulation can also raise the heart function.

In accordance with at least one aspect of the present invention, blocking and/or modulating the signal in the vagus nerve, and/or blocking and/or affecting the histamine response of the vagus nerve, to reduce parasympathetic tone provides an immediate emergency response, much like a defibrillator, in situations of severe asthma attacks or anaphylactic shock, providing immediate temporary dilation of the airways and optionally an increase of heart function until subsequent measures, such as administration of epinephrine, rescue breathing and intubation can be employed. Moreover, the teachings of the present invention permit immediate airway dilation and/or heart function increase to enable subsequent life saving measures that otherwise would be ineffective or impossible due to severe constriction or other physiological effects. Treatment in accordance with the present invention provides bronchodilation and optionally increased heart function for a long enough period of time so that administered medication such as epinephrine has time to take effect before the patient suffocates.

The methods described herein of applying an electrical impulse to a selected region of the vagus nerve may further be refined such that the at least one region may comprise at least one nerve fiber emanating from the patient's tenth cranial nerve (the vagus nerve), and in particular, at least one of the anterior bronchial branches thereof, or alternatively at least one of the posterior bronchial branches thereof. Preferably the impulse is provided to at least one of the anterior pulmonary or posterior pulmonary plexuses aligned along the exterior of the lung. As necessary, the impulse may be directed to nerves innervating only the bronchial tree and lung tissue itself. In addition, the impulse may be directed to a region of the vagus nerve to block and/or modulate both the cardiac and bronchial branches. As recognized by those having skill in the art, this embodiment should be carefully evaluated prior to use in patients known to have preexisting cardiac issues.

Figure 3:
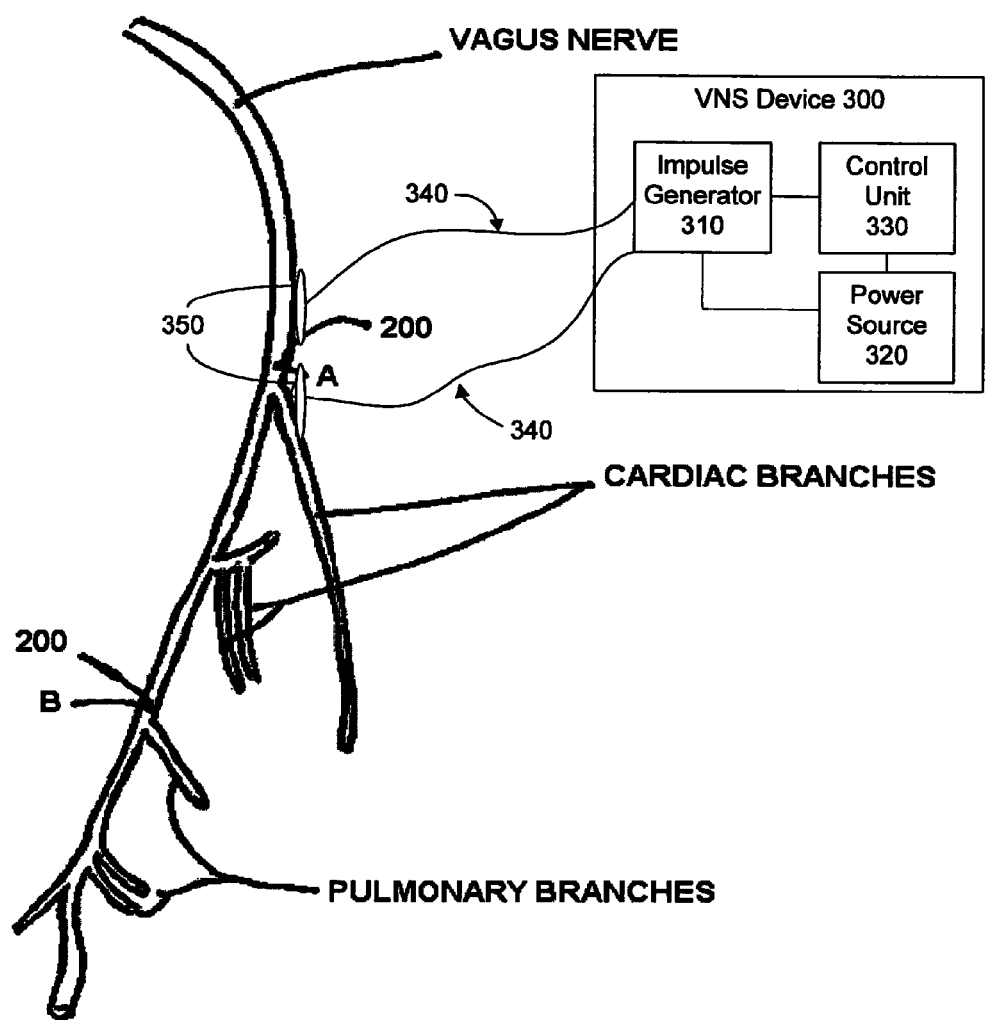
FIG. 3 illustrates a simplified view of the vagus nerve shown in FIGS. 1 and 2.

Further reference is now made to FIG. 3, which illustrates a simplified view of the vagus nerve shown in FIG. 2 and cardiac and pulmonary branches thereof. Also shown is a vagus nerve stimulation (VNS) device 300 for stimulation of the vagus nerve. VNS device 300 is intended for the treatment of bronchial constriction or hypotension associated with anaphylactic shock or asthma. VNS device 300 may include an electrical impulse generator 310; a power source 320 coupled to the electrical impulse generator 310; a control unit 330 in communication with the electrical impulse generator 310 and coupled to the power source 320; and electrodes 340 coupled to the electrical impulse generator 310 for attachment via leads 350 to one or more selected regions 200A, 200B of a vagus nerve 200 of a mammal. The control unit 330 may control the electrical impulse generator 310 for generation of a signal suitable for amelioration of the bronchial constriction or hypotension when the signal is applied via the electrodes 340 to the vagus nerve 200. It is noted that VNS device 300 may be referred to by its function as a pulse generator.

In accordance with one embodiment, one or more electrical impulses are directed to location A on or near the vagus nerve above the cardiac branch. In this embodiment one or more electrical impulses are introduced at the location A to block and/or modulate and/or inhibit upregulation of the parasympathetic tone and effect a dilation of airways and increase in heart function.

In accordance with another embodiment, one or more electrical impulses are directed to location B on or near the vagus nerve below the cardiac branch proximal to the pulmonary branch. In this embodiment one or more electrical impulses are introduced at the location B to block and/or modulate and/or inhibit upregulation of the parasympathetic tone to effect only a dilation of airways.

In patients known to be subject to anaphylactic shock or severe asthma attacks, one or more electrical impulse emitting devices 300 may be implanted in one or more selected regions 200A, 200B of the vagus nerve 200. Device 300 may be percutaneous for emergency applications, wherein device 300 may comprise an electrode 340 powered via an external power source 320.

U.S. patent application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention.

Figure 4:
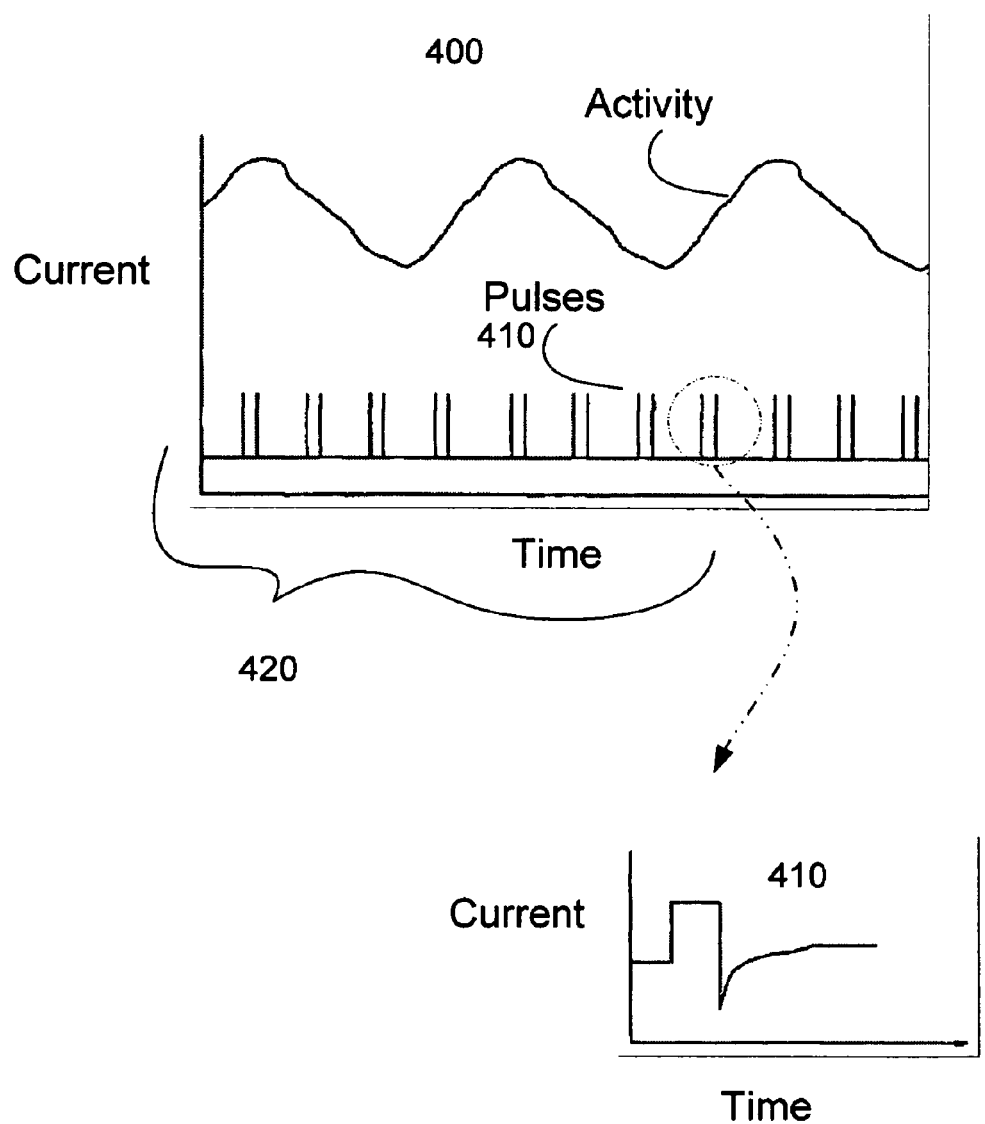
FIG. 4 illustrates an exemplary electrical voltage/current profile for a blocking and/or modulating impulse applied to a portion or portions of the vagus nerve in accordance with an embodiment of the present invention.

FIG. 4 illustrates an exemplary electrical voltage/current profile for a blocking and/or modulating impulse applied to a portion or portions of the vagus nerve in accordance with an embodiment of the present invention.

With reference to FIG. 4, a suitable electrical voltage/current profile 400 for the blocking and/or modulating impulse 410 to the portion or portions 200A, 200B of the vagus nerve 200 may be achieved using a pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the blocking and/or modulating impulse 410 to the nerve 200 via leads 350. For percutaneous use, the VNS device 300 may be available to the surgeon as external emergency equipment. For subcutaneous use, the VNS device 300 may be surgically implanted, such as in a subcutaneous pocket of the abdomen. The VNS device 300 may be powered and/or recharged from outside the body or may have its own power source 320. By way of example, the VNS device 300 may be purchased commercially. The VNS device 300 is preferably programmed with a physician programmer, such as a Model 7432 also available from Medtronic, Inc.

The parameters of the modulation signal 400 are preferably programmable, such as the frequency, amplitude, duty cycle, pulse width, pulse shape, etc. In the case of an implanted pulse generator, programming may take place before or after implantation. For example, an implanted pulse generator may have an external device for communication of settings to the generator. An external communication device may modify the pulse generator programming to improve treatment.

The electrical leads 350 and electrodes 340 are preferably selected to achieve respective impedances permitting a peak pulse voltage in the range from about 0.2 volts to about 20 volts.

The blocking and/or modulating impulse signal 410 preferably has a frequency, an amplitude, a duty cycle, a pulse width, a pulse shape, etc. selected to influence the therapeutic result, namely blocking and/or modulating some or all of the vagus nerve transmissions. For example the frequency may be about 1 Hz or greater, such as between about 25 Hz to 3000 Hz, or between about 1000 Hz to about 2500 Hz. (These are notably higher frequencies than typical nerve stimulation or modulation frequencies.) The modulation signal may have a pulse width selected to influence the therapeutic result, such as about 20 μS or greater, such as about 20 μS to about 1000 μS. The modulation signal may have a peak voltage amplitude selected to influence the therapeutic result, such as about 0.2 volts or greater, such as about 0.2 volts to about 20 volts.

In accordance with a preferred embodiment, VNS devices 300 in accordance with the present invention are provided in the form of a percutaneous or subcutaneous implant that can be reused by an individual.

In accordance with another embodiment, devices in accordance with the present invention are provided in a "pacemaker" type form, in which electrical impulses 410 are generated to a selected region 200A, 200B of the vagus nerve 200 by VNS device 300 on an intermittent basis to create in the patient a lower reactivity of the vagus nerve 200 to upregulation signals.

In accordance with another embodiment, devices 300 in accordance with the present invention are incorporated in an endotracheal tube device to ameliorate bronchospasm during surgery. In a preferred embodiment one or more devices 300 are located in the distal portion of an endotracheal tube to contact selected regions 200A, 200B of the vagus nerve 200 to impart appropriate electrical impulses to dampen reactivity of the vagus nerve 200 to stimulus. In all cases of permanent implantation, however, the implanting surgeon should vary the signal modulated by the control unit 330 and specific location of the lead 350 until the desired outcome is achieved, and should monitor the long-term maintenance of this effect to ensure that adaptive mechanisms in the patient's body do not nullify the intended effects.

In addition, or as an alternative to the devices to implement the modulation unit for producing the electrical voltage/current profile of the blocking and/or modulating impulse to the electrodes, the device disclosed in U.S. patent Publication No.: 2005/0216062 (the entire disclosure of which is incorporated herein by reference), may be employed. U.S. patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

Prior to discussing experimental results, a general approach to treating bronchial constriction in accordance with one or more embodiments of the invention may include a method of (or apparatus for) treating bronchial constriction associated with anaphylactic shock or asthma, comprising applying at least one electrical impulse to one or more selected regions of the vagus nerve of a mammal in need of relief of bronchial constriction.

The method may include: implanting one or more electrodes to the selected regions of the vagus nerve; and applying one or more electrical stimulation signals to the electrodes to produce the at least one electrical impulse, wherein the one or more electrical stimulation signals are of a frequency between about 1 Hz to 3000 Hz, and an amplitude of between about 1-6 volts.

The one or more electrical stimulation signals may be of a frequency between about 750 Hz to 1250 Hz; or between about 15 Hz to 35 Hz. The one or more electrical stimulation signals may be of an amplitude of between about 0.75 to 1.25 volts, preferably about 1.0 volts. The one or more electrical stimulation signals may be one or more of a full or partial sinusoid, square wave, rectangular wave, and/or triangle wave. The one or more electrical stimulation signals may have a pulsed on-time of between about 50 to 500 microseconds, such as about 100, 200 or 400 microseconds.

The polarity of the pulses may be maintained either positive or negative. Alternatively, the polarity of the pulses may be positive for some periods of the wave and negative for some other periods of the wave. By way of example, the polarity of the pulses may be altered about every second.

While upregulating the signal provided by the sympathetic nerves may accomplish the desired treatment effect, the present invention suggests that a more direct route to immediately breaking the cycle of bronchoconstriction or hypotension is via the vagus nerve because the mode of action for the hypersensitivity response in bronchoconstriction or hypotension is at the vagus nerve and not through the sympathetic nerves. Therefore, experiments were performed to identify exemplary methods of how electrical signals can be supplied to the peripheral nerve fibers that innervate and/or control the bronchial smooth muscle to (i) reduce the sensitivity of the muscle to the signals to constrict, and (ii) to blunt the intensity of, or break the constriction once it has been initiated.

In particular, specific signals, selected from within a range of known nerve signals, were applied to the vagus nerves and/or the sympathetic nerves in guinea pigs, to produce selective interruption or reduction in the effects of lung vagal nerve activity leading to attenuation of histamine-induced bronchoconstriction.

Male guinea pigs (400 g) were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves.

Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of frequency, voltage and pulse duration to identity parameters that attenuate responses to i.v. histamine. Bronchoconstriction in response to i.v. histamine is known to be due both to direct airway smooth muscle effects and to stimulation of vagal nerves to release acetylcholine.

At the end of vagal nerve challenges, atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP shows blood pressure, second line AP1 shows airway pressure, third line AP2 shows airway pressure on another sensor, the last line HR is the heart rate derived from the pulses in the blood pressure.

In the first animals, the signal frequency applied was varied from less than 1 Hz through 2,000 Hz, and the voltage was varied from 1V to 12V. Initial indications seemed to show that an appropriate signal was 1,000 Hz, 400 µs, and 6-10V.

Figure 5:
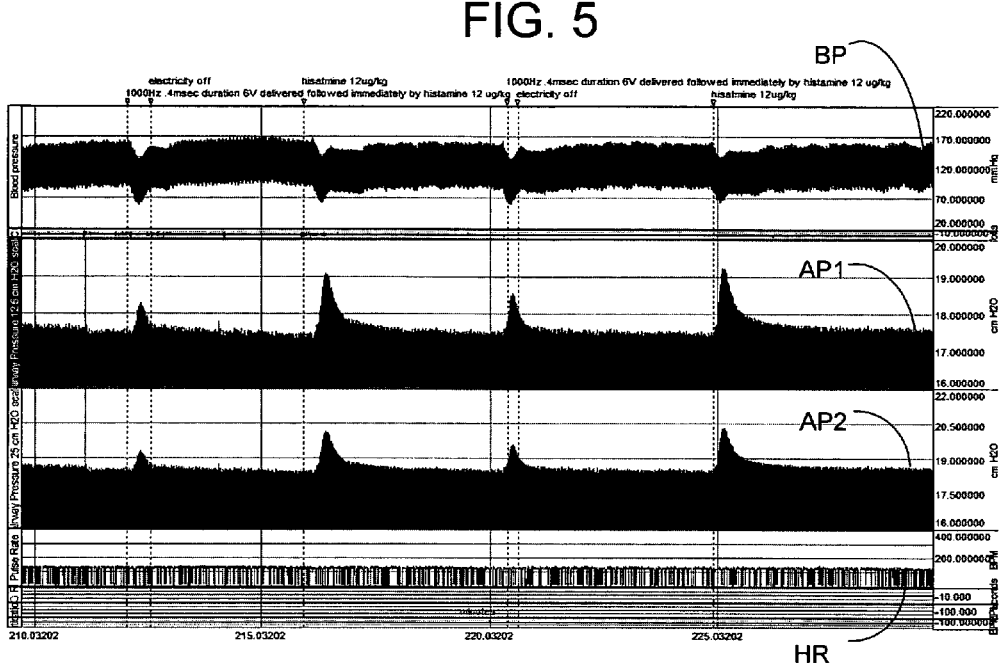
FIGS. 5-14 graphically illustrate exemplary experimental data obtained in accordance with multiple embodiments of the present invention.

FIG. 5 graphically illustrates exemplary experimental data on guinea pig #2. More specifically, the graphs of FIG. 5 show the effect of a 1000 Hz, 400 µS, 6V square wave signal applied simultaneously to both left and right branches of the vagus nerve in guinea pig #2 when injected with 12 µg/kg histamine to cause airway pressure to increase. The first peak in airway pressure is histamine with the electric signal applied to the vagus, the next peak is histamine alone (signal off), the third peak is histamine and signal again, fourth peak is histamine alone again. It is clearly shown that the increase in airway pressure due to histamine is reduced in the presence of the 1000 Hz, 400 µS, 6V square wave on the vagus nerve. The animal's condition remained stable, as seen by the fact that the blood pressure and heart rate are not affected by this electrical signal.

After several attempts on the same animal to continue to reproduce this effect with the 1,000 Hz signal, however, we observed that the ability to continuously stimulate and suppress airway constriction was diminished, and then lost. It appeared that the nerve was no longer conducting. This conclusion was drawn from the facts that (i) there was some discoloration of the nerve where the electrode had been making contact, and (ii) the effect could be resuscitated by moving the lead distally to an undamaged area of the nerve, i.e. toward the organs, but not proximally, i.e., toward the brain. The same thing occurred with animal #3. It has been hypothesized that the effect seen was, therefore, accompanied by a damaging of the nerve, which would not be clinically desirable.

To resolve the issue, in the next animal (guinea pig #4), we fabricated a new set of electrodes with much wider contact area to the nerve. With this new electrode, we started investigating signals from 1 hz to 3,000 Hz again. This time, the most robust effectiveness and reproducibility was found at a frequency of 25 Hz, 400 µs, 1V.

Figure 6:
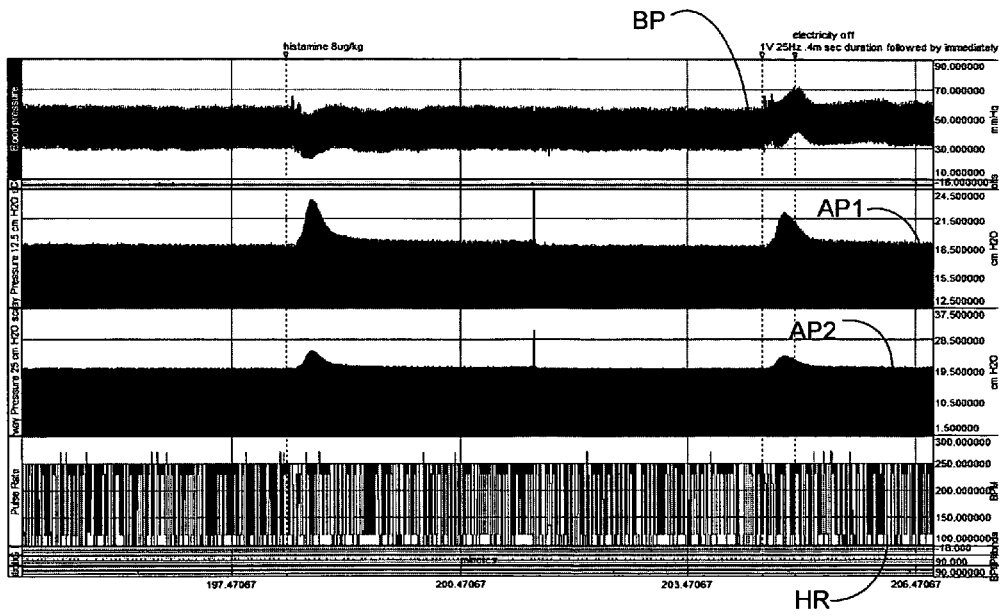

FIG. 6 graphically illustrates exemplary experimental data on guinea pig #5. The graphs of FIG. 6 show the effect of a 25 Hz, 400 µS, 1V square wave signal applied to both left and right vagus nerve in guinea pig #5 when injected with 8 µg/kg histamine to cause airway pressure to increase. The first peak in airway pressure is from histamine alone, the next peak is histamine and signal applied. It is clearly shown that the increase in airway pressure due to histamine is reduced in the presence of the 25 Hz, 400 µS, 1V square wave on the vagus nerve.

Figure 7:
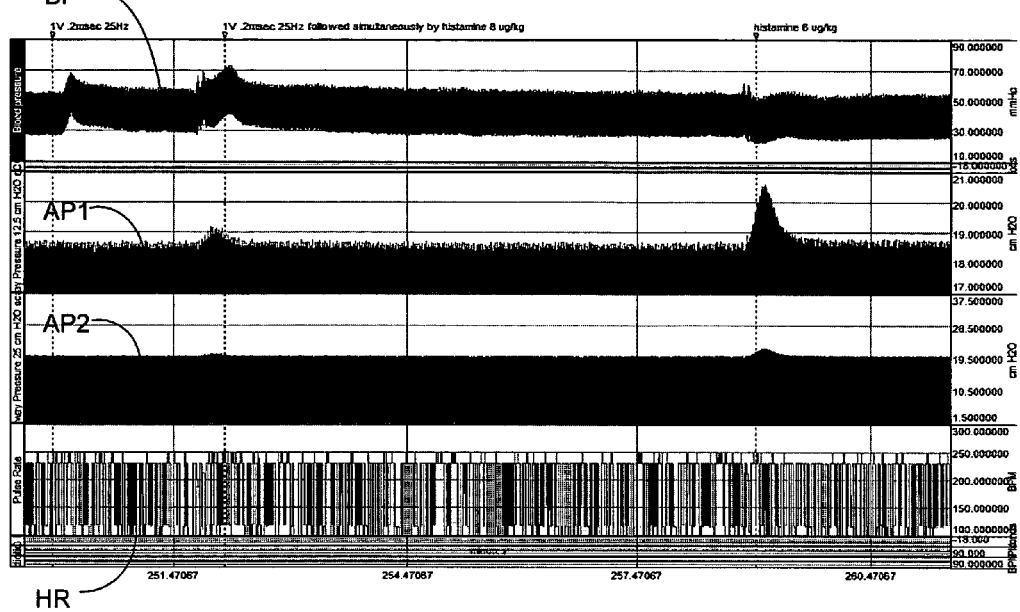

FIG. 7 graphically illustrates additional exemplary experimental data on guinea pig #5. The graphs of FIG. 7 show the effect of a 25 Hz, 200 µS, 1V square wave signal applied to both of the left and right vagus nerves in guinea pig #5 when injected with 8 µg/kg histamine to cause airway pressure to increase. The second peak in airway pressure is from histamine alone, the first peak is histamine and signal applied. It is clearly shown that the increase in airway pressure due to histamine is reduced in the presence of the 25 Hz, 200 µS, 1V square wave on the vagus nerve. It is clear that the airway pressure reduction is even better with the 200 µS pulse width than the 400 µS signal.

Figure 8:
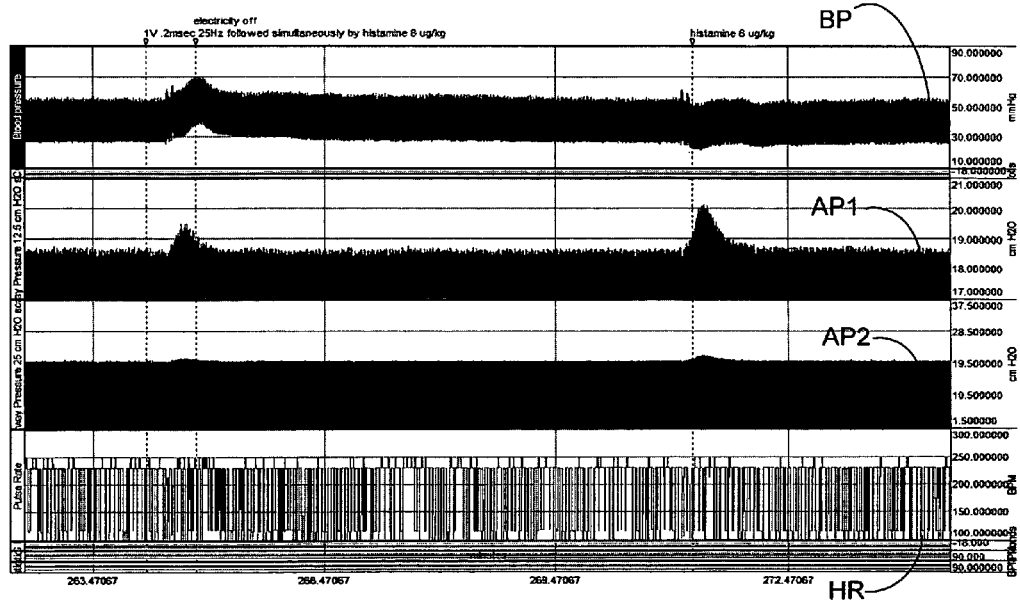

FIG. 8 graphically illustrates further exemplary experimental data on guinea pig #5. The graphs of FIG. 8 show repeatability of the effect seen in the previous graph. The animal, histamine and signal are the same as the graphs in FIG. 7.

It is significant that the effects shown above were repeated several times with this animal (guinea pig #5), without any loss of nerve activity observed. We could move the electrodes proximally and distally along the vagus nerve and achieve the same effect. It was, therefore, concluded that the effect was being achieved without damaging the nerve.

Figure 9:
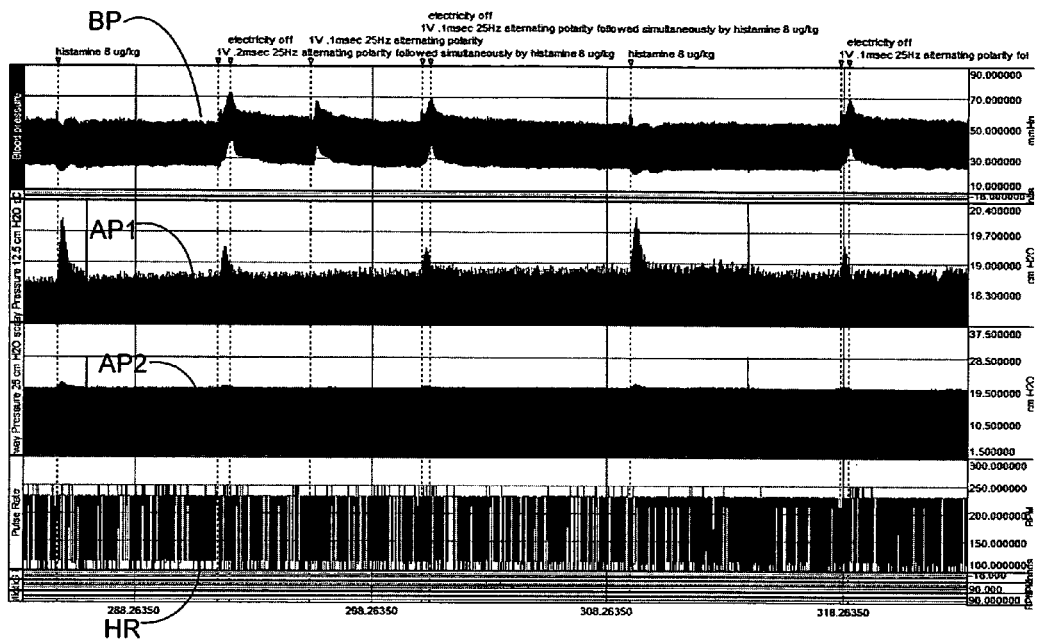

FIG. 9 graphically illustrates subsequent exemplary experimental data on guinea pig #5. The graphs of FIG. 9 show the effect of a 25 Hz, 100 µS, 1V square wave that switches polarity from + to − voltage every second. This signal is applied to both left and right vagus nerve in guinea pig #5 when injected with 8 µg/kg histamine to cause airway pressure to increase. From left to right, the vertical dotted lines coincide with airway pressure events associated with: (1) histamine alone (large airway spike—followed by a very brief manual occlusion of the airway tube); (2) histamine with a 200 µS signal applied (smaller airway spike); (3) a 100 µS electrical signal alone (no airway spike); (4) histamine with a 100 uS signal applied (smaller airway spike again); (5) histamine alone (large airway spike); and (6) histamine with the 100 µS signal applied.

This evidence strongly suggests that the increase in airway pressure due to histamine can be significantly reduced by the application of a 25 Hz, 100 µS, 1V square wave with alternating polarity on the vagus nerve.

Figure 10:
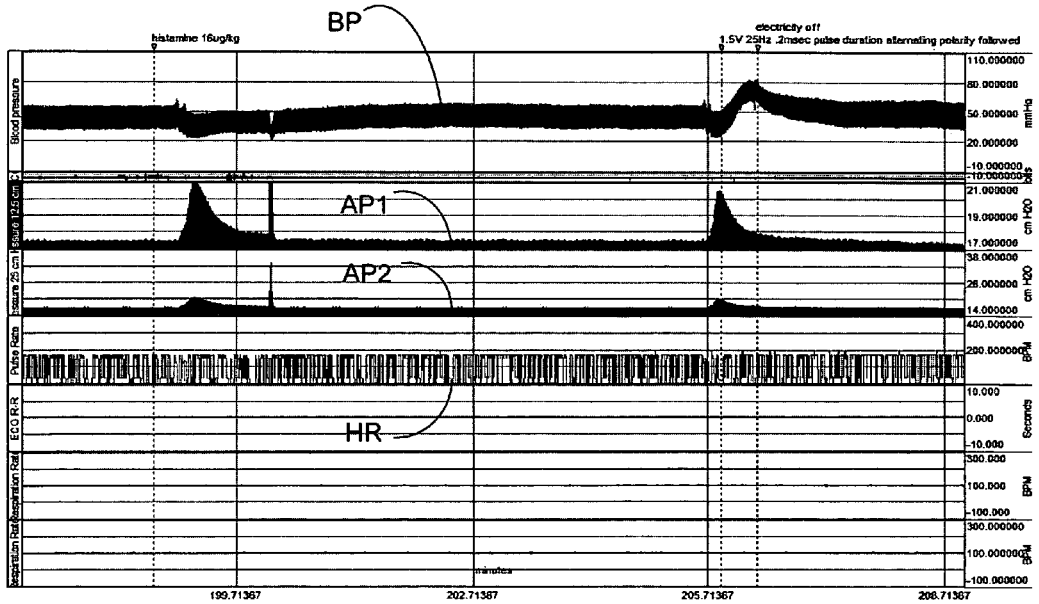

FIG. 10 graphically illustrates exemplary experimental data on guinea pig #6. The graphs in FIG. 10 show the effect of a 25 Hz, 200 µS, 1V square wave that switches polarity from + to − voltage every second. This signal is applied to both left and right vagus nerve in guinea pig #6 when injected with 16 µg/kg histamine to cause airway pressure to increase. (Note that this animal demonstrated a very high tolerance to the effects of histamine, and therefore was not an ideal test subject for the airway constriction effects, however, the animal did provide us with the opportunity to test modification of other signal parameters.)

In this case, the first peak in airway pressure is from histamine alone, the next peak is histamine with the signal applied. It is clearly shown that the increase in airway pressure due to histamine is reduced moderately in its peak, and most definitely in its duration, when in the presence of the 25 Hz, 200 µS, 1V square wave with alternating polarity on the vagus nerve.

Figure 11:
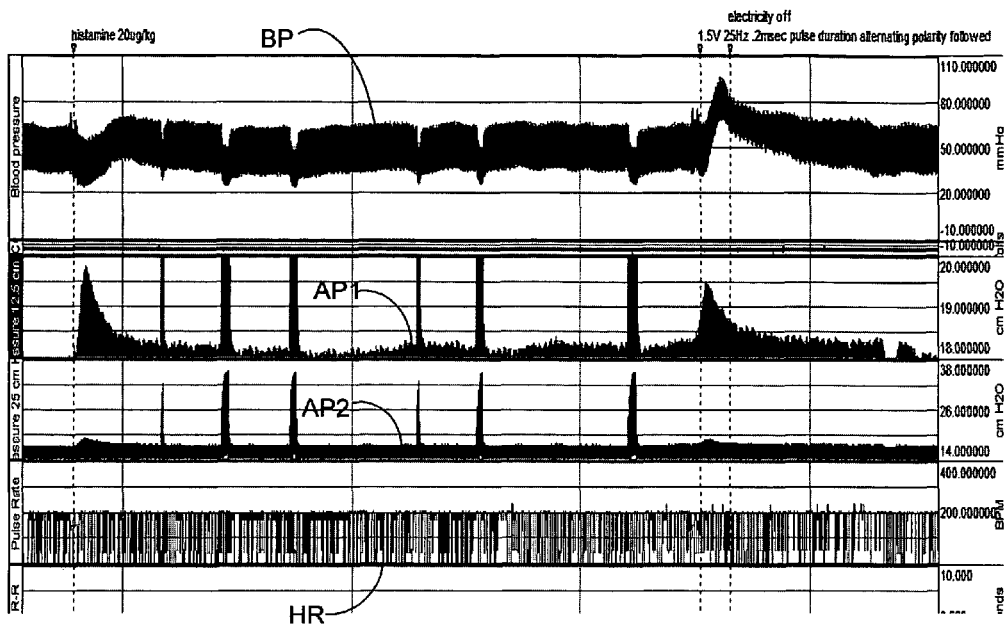

FIG. 11 graphically illustrates additional exemplary experimental data on guinea pig #6. As mentioned above, guinea pig #6 in the graphs of FIG. 10 above needed more histamine than other guinea pigs (16-20 µg/kg vs 8 µg/kg) to achieve the desired increase in airway pressure. Also, the beneficial effects of the 1V signal were less pronounced in pig #6 than in #5. Consequently, we tried increasing the voltage to 1.5V. The first airway peak is from histamine alone (followed by a series of manual occlusions of the airway tube), and the second peak is the result of histamine with the 1.5V, 25 Hz, 200 µS alternating polarity signal. The beneficial effects are seen with slightly more impact, but not substantially better than the 1V.

Figure 12:
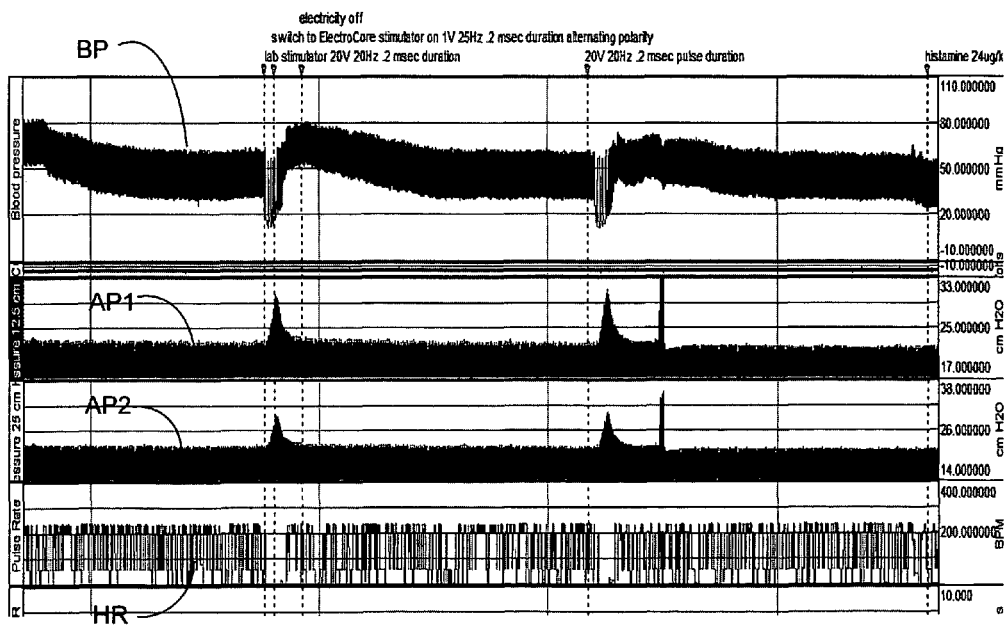

FIG. 12 graphically illustrates further exemplary experimental data on guinea pig #6. Since guinea pig #6 was losing its airway reaction to histamine, we tried to determine if the 25 Hz, 200 µS, 1V, alternating polarity signal could mitigate the effects of a 20V, 20 Hz airway pressure stimulating signal that has produced a simulated asthmatic response. The first airway peak is the 20V, 20 Hz stimulator signal applied to increase pressure, then switched over to the 25 Hz, 200 µS, 1V, alternating polarity signal. The second peak is the 20V, 20 Hz signal alone. The first peak looks modestly lower and narrower than the second. The 25 Hz, 200 µS, 1V signal may have some beneficial airway pressure reduction after electrical stimulation of airway constriction.

Figure 13:
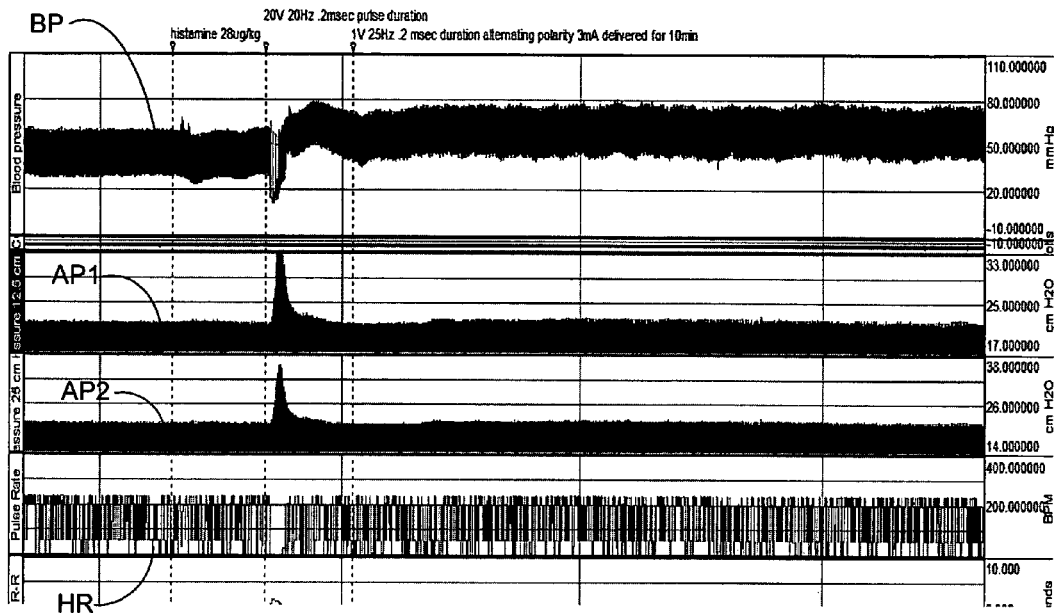

FIG. 13 graphically illustrates subsequent exemplary experimental data. On guinea pig #6 we also investigated the effect of the 1V, 25 Hz, and 200 µS alternating polarity signal. Even after application of the signal for 10 minutes continuously, there was no loss of nerve conduction or signs of damage.

Figure 14:
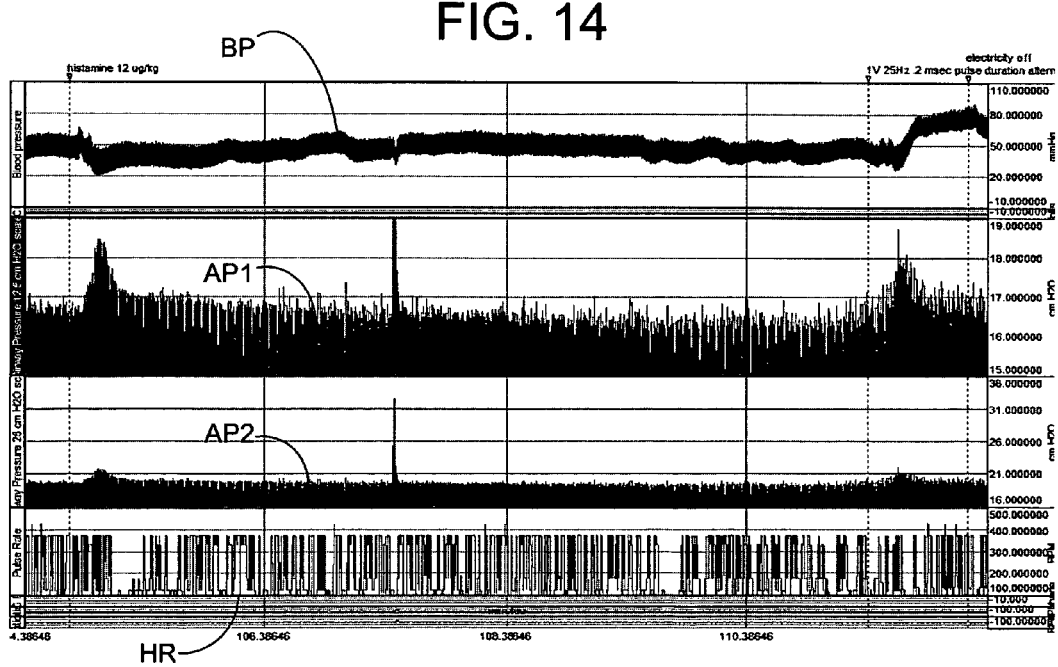

FIG. 14 graphically illustrates exemplary experimental data on guinea pig #8. The graph below shows the effect of a 25 Hz, 200 µS, 1V square wave that switches polarity from + to − voltage every second. This signal is applied to both left and right vagus nerve in guinea pig #8 when injected with 12 µg/kg histamine to cause airway pressure to increase. The first peak in airway pressure is from histamine alone, the next peak is histamine with the signal applied. It is clearly shown that the increase in airway pressure due to histamine is reduced in the presence of the 25 Hz, 200 µS, 1V square wave with alternating polarity on the vagus nerve. We have reproduced this effect multiple times, on 4 different guinea pigs, on 4 different days.

The airway constriction induced by histamine in guinea pigs can be significantly reduced by applying appropriate electrical signals to the vagus nerve.

We found at least 2 separate frequency ranges that have this effect. At 1000 Hz, 6V, 400 µS the constriction is reduced, but there is evidence that this is too much power for the nerve to handle. This may be mitigated by different electrode lead design in future tests. Different types of animals also may tolerate differently differing power levels.

With a 25 Hz, 1V, 100-200 µS signal applied to the vagus nerve, airway constriction due to histamine is significantly reduced. This has been repeated on multiple animals many times. There is no evidence of nerve damage, and the power requirement of the generator is reduced by a factor of between 480 (40×6×2) and 960 (40×6×4) versus the 1000 Hz, 6V, 400 µS signal.

Application of the signal to the vagus nerve appears to have some effects lasting long after the signal is removed. Specific, repeatable experimentation may be done to substantiate these longer lasting effects. Additional testing on the guinea pig model may quantify the extent to which longer lasting effects remain after stimulation is removed.

Additional tests may determine also if the reduction in airway pressure is due primarily to one branch of the vagus nerve, i.e., the left branch or the right branch.

In U.S. patent application Ser. No. 10/990,938 filed Nov. 17, 2004 (Publication Number US2005/0125044A1), Kevin J. Tracey proposes a method of treating many diseases including, among others, asthma, anaphylactic shock, sepsis and septic shock by electrical stimulation of the vagus nerve. However, the examples in the Tracey application use an electrical signal that is 1 to 5V, 1 Hz and 2 mS to treat endotoxic shock, and no examples are shown that test the proposed method on an asthma model, an anaphylactic shock model, or a sepsis model. The applicants of the present application performed additional testing to determine if Tracey's proposed method has any beneficial effect on asthma or blood pressure in the model that shows efficacy with the method used in the present application. The applicants of the present application sought to determine whether Tracey's signals can be applied to the vagus nerve to attenuate histamine-induced bronchoconstriction and increase in blood pressure in guinea pigs.

Male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 µg/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 1 to 5 volts, 1 Hz, 2 mS to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP (red) shows blood pressure, second line AP1 shows airway pressure, third line AP2 shows airway pressure on another sensor, the last line HR is the heart rate derived from the pulses in the blood pressure.

Figure 15:
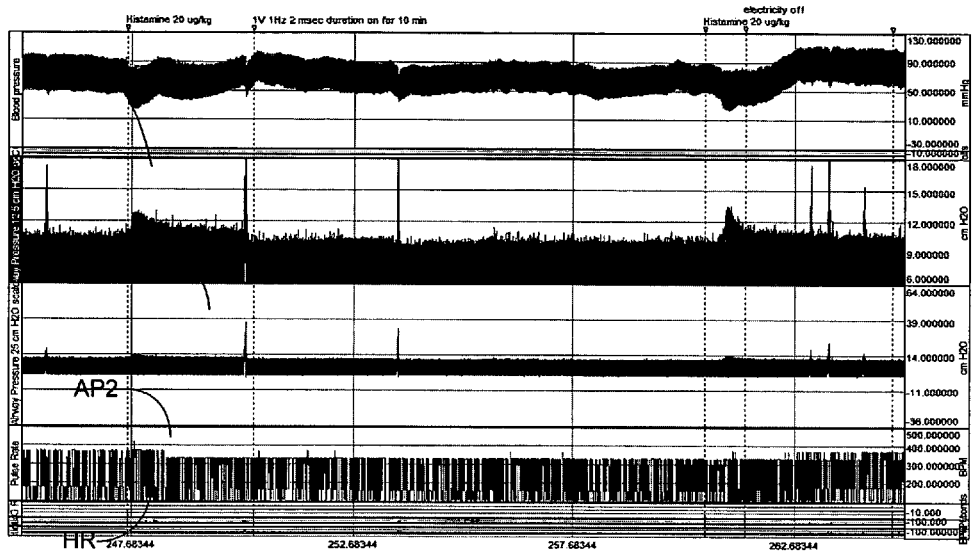
FIGS. 15-20 graphically illustrate the inability of signals taught by U.S. patent application Ser. No. 10/990,938 to achieve the results of the present invention.

FIG. 15 graphically illustrates exemplary experimental data from a first experiment on another guinea pig. The graph shows the effects of Tracey's 1V, 1 Hz, 2 mS waveform applied to both vagus nerves on the guinea pig. The first peak in airway pressure is from histamine alone, after which Tracey's signal was applied for 10 minutes as proposed in Tracey's patent application. As seen from the second airway peak, the signal has no noticeable effect on airway pressure. The animal's vital signs actually stabilized, seen in the rise in blood pressure, after the signal was turned off.

Figure 16:
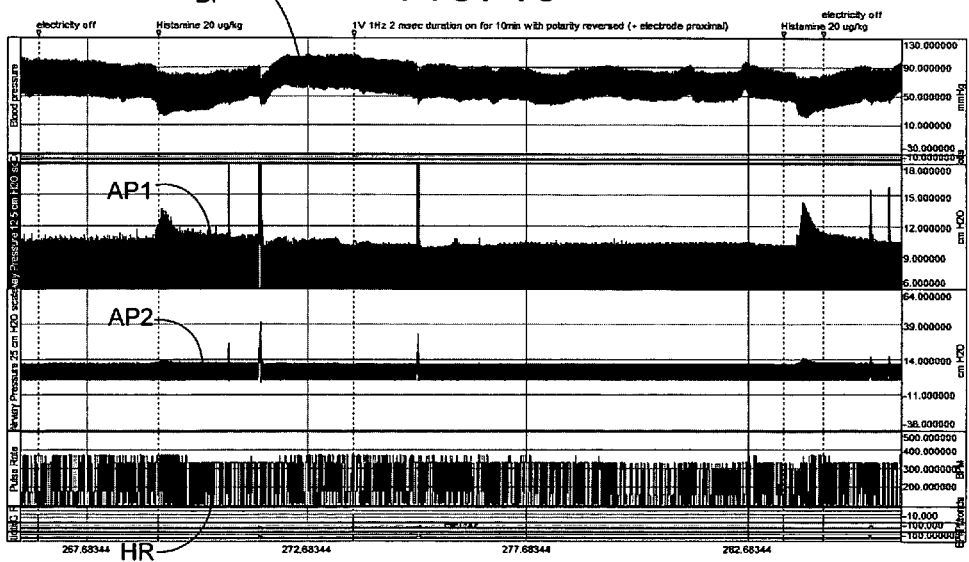

FIG. 16 graphically illustrates exemplary experimental data from a second experiment on the guinea pig in FIG. 15. The graph shows the effects of Tracey's 1V, 1 Hz, 2 mS waveform with the polarity reversed (Tracey did not specify polarity in the patent application) applied to both vagus nerves on the guinea pig. Again, the signal has no beneficial effect on airway pressure. In fact, the second airway peak from the signal and histamine combination is actually higher than the first peak of histamine alone.

Figure 17:
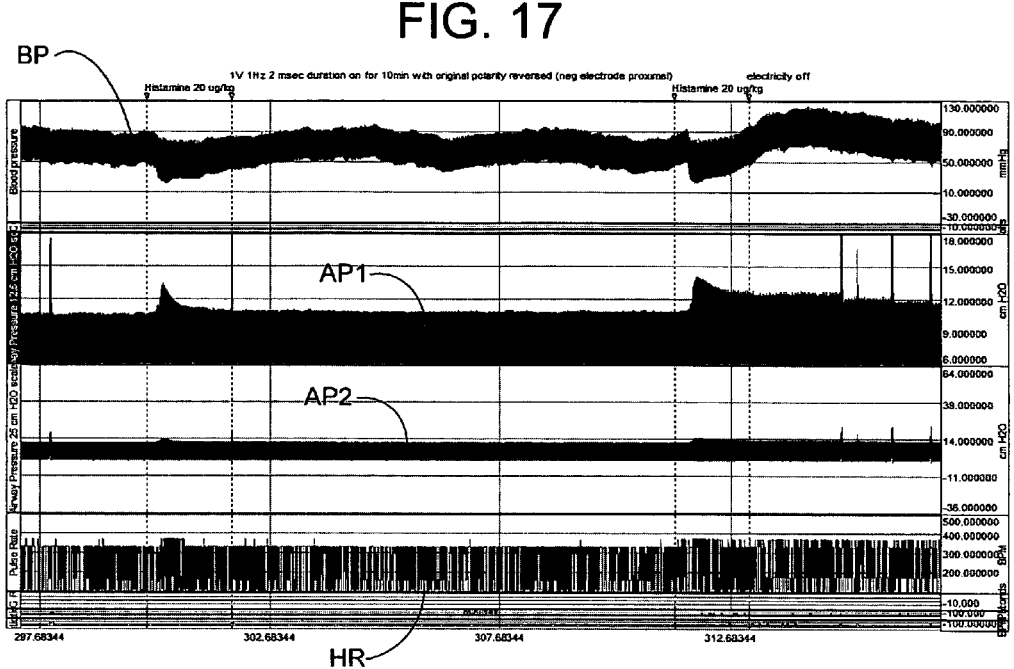

FIG. 17 graphically illustrates exemplary experimental data from a third experiment on the guinea pig in FIG. 15. The graph shows the effects of Tracey's 1V, 1 Hz, 2 mS waveform applied to both vagus nerves on the guinea pig. Again, the signal has no beneficial effect on airway pressure. Instead, it increases airway pressure slightly throughout the duration of the signal application.

Figure 18:
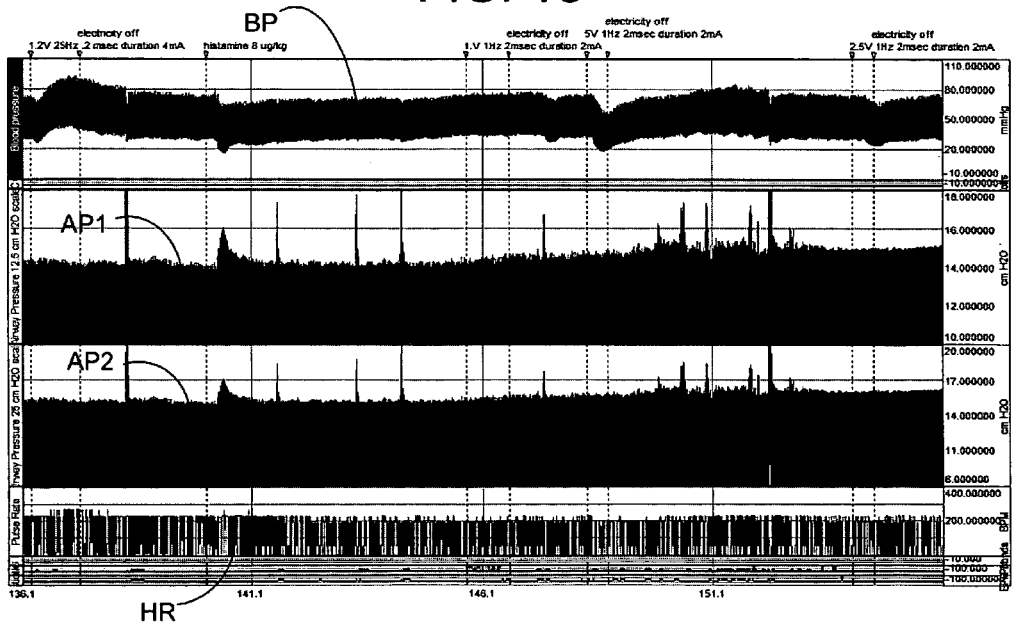

FIG. 18 graphically illustrates additional exemplary experimental data from an experiment on a subsequent guinea pig. The graph shows, from left to right, application of the 1.2V, 25 Hz, 0.2 mS signal disclosed in the present application, resulting in a slight decrease in airway pressure in the absence of additional histamine. The subsequent three electrical stimulation treatments are 1V, 5V, and 2.5V variations of Tracey's proposed signal, applied after the effects of a histamine application largely had subsided. It is clear that the Tracey signals do not cause a decrease in airway pressure, but rather a slight increase, which remained and progressed over time.

Figure 19:
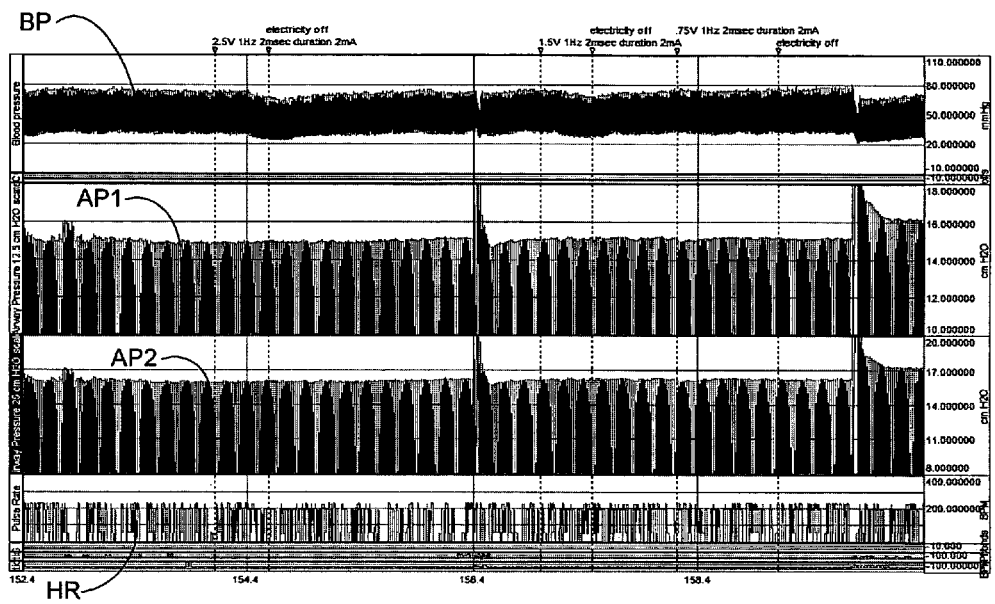

FIG. 19 graphically illustrates further exemplary experimental data from additional experiments using signals within the range of Tracey's proposed examples. None of the signals proposed by Tracey had any beneficial effect on airway pressure. Factoring in a potential range of signals, one experiment used 0.75V, which is below Tracey's proposed range, but there was still no beneficial effect on airway pressure.

Figure 20:
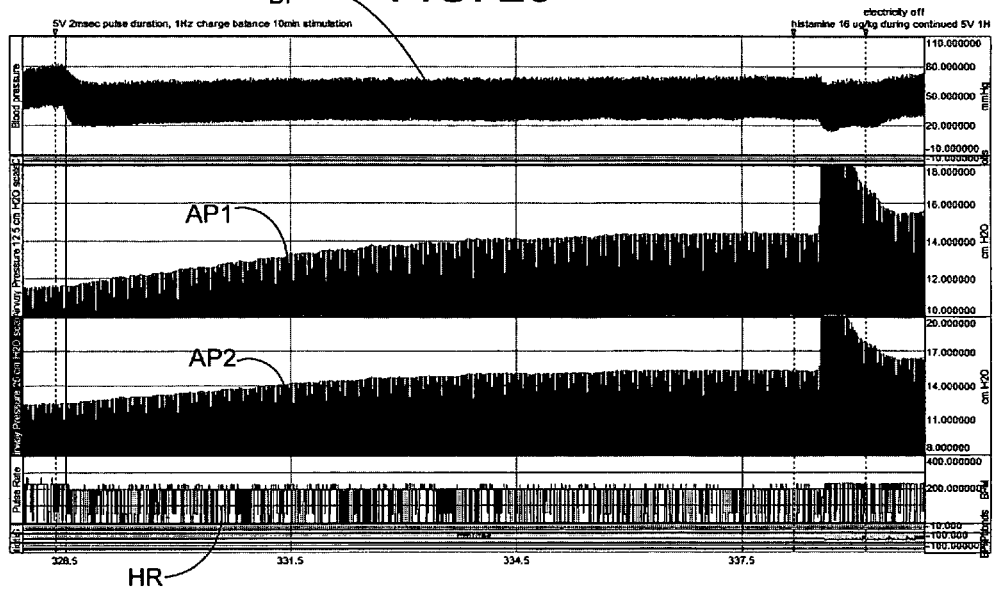

FIG. 20 graphically illustrates exemplary experimental data from subsequent experiments showing the effect of Tracey's 5V, 1 Hz, 2 mS signal, first without and then with additional histamine. It is clear that the airway pressure increase is even greater with the signal, as the airway pressure progressively increased during the course of signal application. Adding the histamine after prolonged application of the Tracey signal resulted in an even greater increase in airway pressure.

The full range of the signal proposed by Tracey in his patent application was tested in the animal model of the present application. No reduction in airway pressure was seen. Most of the voltages resulted in detrimental increases in airway pressure and detrimental effects to vital signs, such as decreases in blood pressure.

Treatment Approach 2

Figure 21:
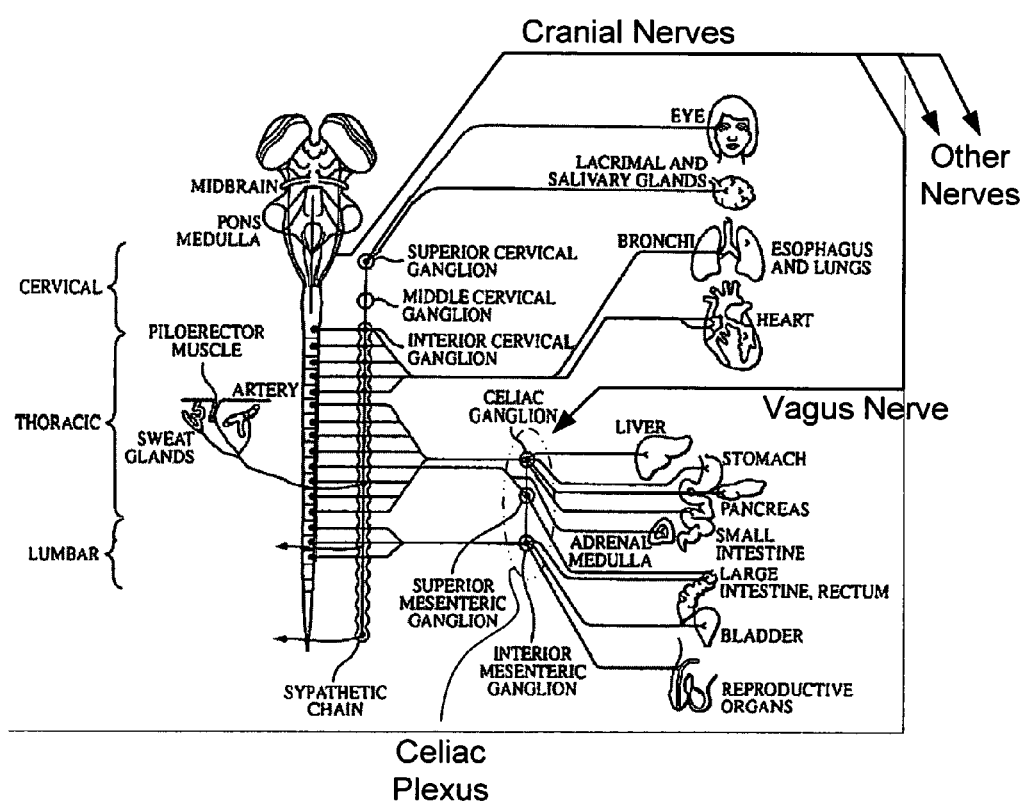
FIG. 21 is a schematic diagram of the human autonomic nervous system, illustrating sympathetic fibers, spinal nerve root fibers, and cranial nerves.
Figure 22:
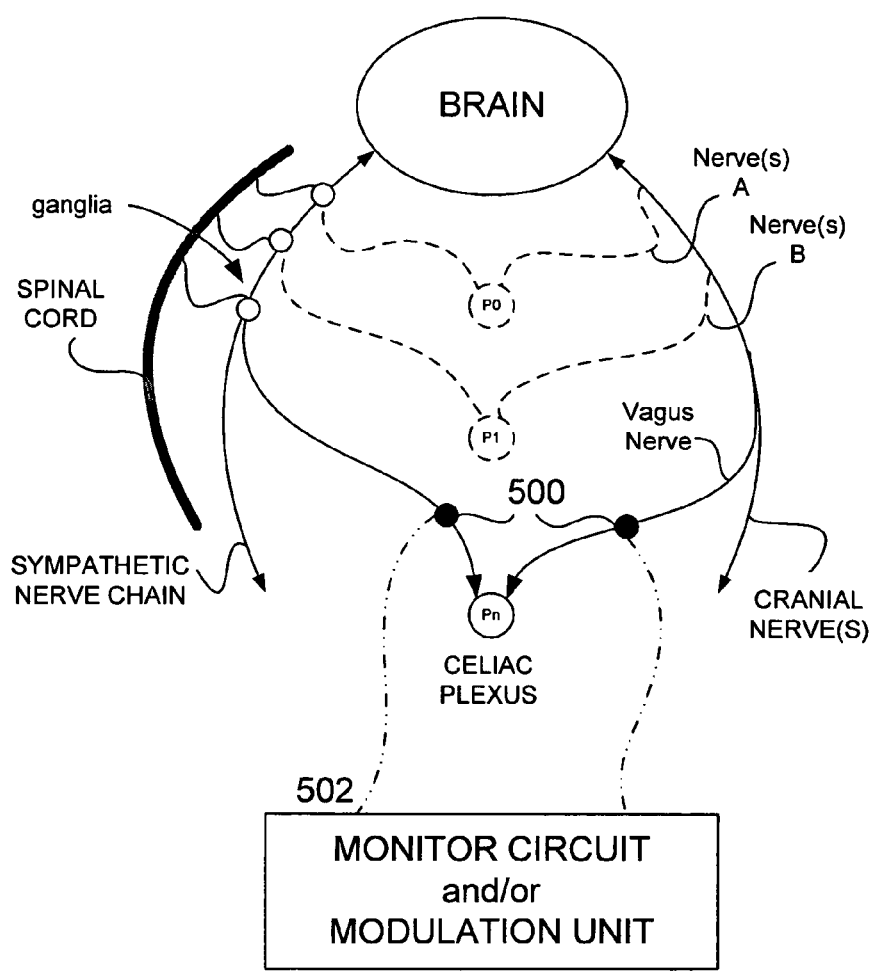
FIG. 22 is a further schematic diagram of the human autonomic nervous system and a modulation system therefore in accordance with one or more embodiments of the present invention.

With reference to the drawings wherein like numerals indicate like elements there are shown in FIGS. 21 and 22 schematic diagrams of the human autonomic nervous system, including sympathetic fibers, parasympathetic fibers, and cerebral nerves.

The sympathetic nerve fibers, along with many of the spinal cord's nerve root fibers, and the cranial nerves that innervate tissue in the thoracic and abdominal cavities are sometimes referred to as the autonomic, or vegetative, nervous system. The sympathetic, spinal, and cranial nerves all have couplings to the central nervous system, generally in the primitive regions of the brain, however, these components have direct effects over many regions of the brain, including the frontal cortex, thalamus, hypothalamus, hippocampus, and cerebellum. The central components of the spinal cord and the sympathetic nerve chain extend into the periphery of the autonomic nervous system from their cranial base to the coccyx, essentially passing down the entire spinal column, including the cervical, thoracic and lumbar regions. The sympathetic chain extends on the anterior of the column, while the spinal cord components pass through the spinal canal. The cranial nerves, the one most innervating of the rest of the body being the vagus nerve, passes through the dura mater into the neck, and then along the carotid and into the thoracic and abdominal cavities, generally following structures like the esophagus, the aorta, and the stomach wall.

Because the autonomic nervous system has both afferent and efferent components, modulation of its fibers can affect both the end organs (efferent) as well as the brain structure to which the afferents fibers are ultimately coupled within the brain.

Although sympathetic and cranial fibers (axons) transmit impulses producing a wide variety of differing effects, their component neurons are morphologically similar. They are smallish, ovoid, multipolar cells with myelinated axons and a variable number of dendrites. All the fibers form synapses in peripheral ganglia, and the unmyelinated axons of the ganglionic neurons convey impulses to the viscera, vessels and other structures innervated. Because of this arrangement, the axons of the autonomic nerve cells in the nuclei of the cranial nerves, in the thoracolumbar lateral comual cells, and in the gray matter of the sacral spinal segments are termed preganglionic sympathetic nerve fibers, while those of the ganglion cells are termed postganglionic sympathetic nerve fibers. These postganglionic sympathetic nerve fibers converge, in small nodes of nerve cells, called ganglia that lie alongside the vertebral bodies in the neck, chest, and abdomen. The effects of the ganglia as part of the autonomic system are extensive. Their effects range from the control of insulin production, cholesterol production, bile production, satiety, other digestive functions, blood pressure, vascular tone, heart rate, sweat, body heat, blood glucose levels, and sexual arousal.

The parasympathetic group lies predominately in the cranial and cervical region, while the sympathetic group lies predominantly in the lower cervical, and thoracolumbar and sacral regions. The sympathetic peripheral nervous system is comprised of the sympathetic ganglia that are ovoid/bulb like structures (bulbs) and the paravertebral sympathetic chain (cord that connects the bulbs). The sympathetic ganglia include the central ganglia and the collateral ganglia.

The central ganglia are located in the cervical portion, the thoracic portion, the lumbar portion, and the sacral portion. The cervical portion of the sympathetic system includes the superior cervical ganglion, the middle cervical ganglion, and the interior cervical ganglion.

The thoracic portion of the sympathetic system includes twelve ganglia, five upper ganglia and seven lower ganglia. The seven lower ganglia distribute filaments to the aorta, and unite to form the greater, the lesser, and the lowest splanchnic nerves. The greater splanchnic nerve (splanchnicus major) is formed by branches from the fifth to the ninth or tenth thoracic ganglia, but the fibers in the higher roots may be traced upward in the sympathetic trunk as far as the first or second thoracic ganglion. The greater splanchnic nerve descends on the bodies of the vertebrae, perforates the crus of the diaphragm, and ends in the celiac ganglion of the celiac plexus.

The lesser splanchnic nerve (splanchnicus minor) is formed by filaments from the ninth and tenth, and sometimes the eleventh thoracic ganglia, and from the cord between them. The lesser splanchnic nerve pierces the diaphragm with the preceding nerve, and joins the aorticorenal ganglion. The lowest splanchnic nerve (splanchnicus imus) arises from the last thoracic ganglion, and, piercing the diaphragm, ends in the renal plexus.

The lumbar portion of the sympathetic system usually includes four lumbar ganglia, connected together by interganglionic cords. The lumbar portion is continuous above, with the thoracic portion beneath the medial lumbocostal arch, and below with the pelvic portion behind the common iliac artery. Gray rami communicantes pass from all the ganglia to the lumbar spinal nerves. The first and second, and sometimes the third, lumbar nerves send white rami communicantes to the corresponding ganglia.

The sacral portion of the sympathetic system is situated in front of the sacrum, medial to the anterior sacral foramina. The sacral portion includes four or five small sacral ganglia, connected together by interganglionic cords, and continuous above with the abdominal portion. Below, the two pelvic sympathetic trunks converge, and end on the front of the coccyx in a small ganglion.

The collateral ganglia include the three great gangliated plexuses, called, the cardiac, the celiac (solar or epigastric), and the hypogastric plexuses. The great plexuses are respectively situated in front of the vertebral column in the thoracic, abdominal, and pelvic regions. They consist of collections of nerves and ganglia; the nerves being derived from the sympathetic trunks and from the cerebrospinal nerves. They distribute branches to the viscera.

Although all of the great plexuses (and their sub-parts) are of interest in accordance with various embodiments of the present invention, by way of example, the celiac plexus is shown in FIGS. 21 and 22 in more detail. The celiac plexus is the largest of the three great sympathetic plexuses and is located at the upper part of the first lumbar vertebra. The celiac plexus is composed of the celiac ganglia and a network of nerve fibers uniting them together. The celiac plexus and the ganglia receive the greater and lesser splanchnic nerves of both sides and some filaments from the right vagus nerve. The celiac plexus gives off numerous secondary plexuses along the neighboring arteries. The upper part of each celiac ganglion is joined by the greater splanchnic nerve, while the lower part, which is segmented off and named the aorticorenal ganglion, receives the lesser splanchnic nerve and gives off the greater part of the renal plexus.

The secondary plexuses associated with the celiac plexus consist of the phrenic, hepatic, lineal, superior gastric, suprarenal, renal, spermatic, superior mesenteric, abdominal aortic, and inferior mesenteric. The phrenic plexus emanates from the upper part of the celiac ganglion and accompanies the inferior phrenic artery to the diaphragm, with some filaments passing to the suprarenal gland and branches going to the inferior vena cava, and the suprarenal and hepatic plexuses. The hepatic plexus emanates from the celiac plexus and receives filaments from the left vagus and right phrenic nerves. The hepatic plexus accompanies the hepatic artery and ramifies upon its branches those of the portal vein in the substance of the liver. Branches from hepatic plexus accompany the hepatic artery, the gastroduodenal artery, and the right gastroepiploic artery along the greater curvature of the stomach.

The lienal plexus is formed from the celiac plexus, the left celiac ganglion, and from the right vagus nerve. The lienal plexus accompanies the lienal artery to the spleen, giving off subsidiary plexuses along the various branches of the artery.

The superior gastric plexus accompanies the left gastric artery along the lesser curvature of the stomach, and joins with branches from the left vagus nerve. The suprarenal plexus is formed from the celiac plexus, from the celiac ganglion, and from the phrenic and greater splanchnic nerves. The suprarenal plexus supplies the suprarenal gland. The renal plexus is formed from the celiac plexus, the aorticorenal ganglion, and the aortic plexus, and is joined by the smallest splanchnic nerve. The nerves from the suprarenal plexus accompany the branches of the renal artery into the kidney, the spermatic plexus, and the inferior vena cava.

The spermatic plexus is formed from the renal plexus and aortic plexus. The spermatic plexus accompanies the internal spermatic artery to the testis (in the male) and the ovarian plexus, the ovary, and the uterus (in the female). The superior mesenteric plexus is formed from the lower part of the celiac plexus and receives branches from the right vagus nerve.

The superior mesenteric plexus surrounds the superior mesenteric artery and accompanies it into the mesentery, the pancreas, the small intestine, and the great intestine. The abdominal aortic plexus is formed from the celiac plexus and ganglia, and the lumbar ganglia. The abdominal aortic plexus is situated upon the sides and front of the aorta, between the origins of the superior and inferior mesenteric arteries, and distributes filaments to the inferior vena cava. The inferior mesenteric plexus is formed from the aortic plexus. The inferior mesenteric plexus surrounds the inferior mesenteric artery, the descending and sigmoid parts of the colon and the rectum.

While the sympathetic and parasympathetic nervous system extends between the brain and the great plexuses, the cranial nerves extend between the brain and the great plexuses along other paths. For example, as best seen in FIG. 22, the sympathetic and parasympathetic nerves extend between the brain the celiac plexus along a first portion of a "circuit," while the vagus nerve extends between the brain the celiac plexus along a second portion of the same circuit.

There are twelve pairs of cranial nerves, namely: the olfactory, optic, oculomotor, trochlear, trigeminal, abducent, facial, acoustic, glossopharyngeal, vagus, accessory, and hypoglossal. The nuclei of origin of the motor nerves and the nuclei of termination of the sensory nerves are brought into relationship with the cerebral cortex.

Although all of the cranial nerves are of interest in accordance with various embodiments of the present invention, by way of example, the vagus nerve is shown in FIGS. 21 and 22 in more detail. The vagus nerve is composed of motor and sensory fibers and is of considerable interest in connection with various embodiments of the present invention because it has a relatively extensive distribution than the other cranial nerves and passes through the neck and thorax to the abdomen. The vagus nerves leaves the cranium and is contained in the same sheath of dura mater with the accessory nerve. The vagus nerve passes down the neck within the carotid sheath to the root of the neck. On the right side, the nerve descends by the trachea to the back of the root of the lung, where it spreads out in the posterior pulmonary plexus. From the posterior pulmonary plexus, two cords descend on the esophagus and divide to form the esophageal plexus. The branches combine into a single cord, which runs along the back of the esophagus, enters the abdomen, and is distributed to the posteroinferior surface of the stomach, joining the left side of the celiac plexus, and sending filaments to the lienal plexus.

On the left side, the vagus nerve enters the thorax, crosses the left side of the arch of the aorta, and descends behind the root of the left lung, forming the posterior pulmonary plexus. From posterior pulmonary plexus, the vagus nerve extends along the esophagus, to the esophageal plexus, and then to the stomach. The vagus nerve branches over the anterosuperior surface of the stomach, the fundus, and the lesser curvature of the stomach.

The branches of distribution of the vagus nerve are as follows: the auricular, the superior laryngeal, the recurrent, the superior cardiac, the inferior cardiac, the anterior bronchial, the posterior bronchial, the esophageal, the celiac, and the hepatic. Although all of the branches of the vagus nerve are of interest in accordance with various embodiments of the invention, the gastric branches and the celiac branches are believed to be of notable interest. The gastric branches are distributed to the stomach, where the right vagus nerve forms the posterior gastric plexus on the postero-inferior surface of the stomach and the left vagus nerve forms the anterior gastric plexus on the antero-superior surface of the stomach. The celiac branches are mainly derived from the right vagus nerve, which enter the celiac plexus and supply branches to the pancreas, spleen, kidneys, suprarenal bodies, and intestine.

One or more embodiments of the present invention provide for one or more methods of treating physiological disorders by at least one of monitoring and modulating one or more nerves and/or one or more muscles on both sides of a particular plexus. Although the various embodiments of the invention are not limited by any particular theory of operation, it is believed that advantages are obtained when the disorder is associated with organs and/or musculature enervated by the nerves entering or leaving the given plexus. For example, it is believed that disorders associated with bronchial restriction (e.g. asthma, anaphylaxis, etc.) may be better treated through electronic monitoring and/or electro-modulation of the nerves and/or musculature on both sides of the cervical ganglion (and/or the esophageal plexus). In particular, it is believed that electrical (or chemical) modulation of: (i) one or more of the sympathetic or parasympathetic nerves (discussed above) on the one side of the appropriate plexus; and (ii) one or more of the vagus nerves (also discussed above) on the other side of the appropriate plexus, will improve the therapeutic effect on one or more pathologies.

Further reference is now made to FIG. 23, which illustrates a process flow of steps or actions, one or more of which may be carried out in accordance with one or more embodiments of the present invention. At action 550, one or more electrodes 500 are implanted on or near at least one of the sympathetic or parasympathetic nerves on one side of a target plexus, such as the celiac plexus. On or more further electrodes 500 are implanted on or near at least one of the cranial nerves entering or leaving the target plexus, or on or near at least one of the muscles enervated by such nerves. The electrodes 500 may be configured as monopolar electrodes, with one electrode 500 per lead, or as multipolar electrodes, with more than one electrode 500 per lead. Preferably, the electrodes 500 are made from a biocompatible conductive material such as platinum-iridium. Any of the known electrodes and leads may be used for this purpose (such as from Medtronic, Model 4300). The electrodes 500 are attached to the electrical leads prior to implantation and navigated to a point near the desired modulation site. The electrical leads and electrodes 500 may be surgically inserted into the patient using a surgical technique, such as laparotomy or laparoscopy, with proximal ends of the leads located near the modulation unit 502 and distal ends located near the desired modulation site.

At action 550 simultaneous monitoring of the nerve and/or muscle activity on both sides of the target plexus is performed using the monitor circuit 502. Any of the known equipment operable to receive electrical signaling from the electrodes 500 and to produce graphic and/or tabular data therefrom may be employed. It is desirable that the monitor circuit 502 and/or a computer associated therewith is capable of correlating and/or analyzing the received data to identify abnormalities in the activity of the nerves and/or muscles (action 554) or to identify a desired activity of the nerves and/or muscles (action 556) to achieve the therapeutic effect. For example, if a bronchial disorder (e.g., asthma) were to be treated, the measured activity of the nerves and/or muscles of the patient may indicate an abnormal bronchial restriction profile. If so, a desired profile may be formulated, which if achieved through modulation of the nerves and/or muscles would result in a reduced desire to eat on the part of the patient.

At action 558, the modulation unit 502 is preferably programmed to modulate the nerves and/or muscles on one or both sides of the target plexus to achieve the therapeutic result (action 560). The modulation may be achieved through electrical and/or chemical intervention. In the case of electrical modulation, the preferred effect may be to stimulate or reversibly block nervous and or muscular tissue. Use of the term block means disruption, modulation, and/or inhibition of nerve impulse transmission and/or muscular flexion and inhibition. Abnormal regulation can result in an excitation of the pathways or a loss of inhibition of the pathways, with the net result being an increased perception or response. Therapeutic measures can be directed towards either blocking the transmission; of signals or stimulating inhibitory feedback. Electrical stimulation permits such stimulation of the target neural structures and, equally importantly, prevents the total destruction of the nervous system. Additionally, electrical stimulation parameters can be adjusted so that benefits are maximized and side effects are minimized.

The electrical voltage/current profile of the modulation signal to the electrodes 500 (and thus the nerves/muscles) may be achieved using a pulse generator (such as that discussed above with respect to FIG. 4). In a preferred embodiment, the modulation unit 502 includes a power source, a processor, a clock, a memory, etc. to produce a pulse train to the electrodes 500. The parameters of the modulation signal are preferably programmable (action 558), such as the frequency, amplitude, duty cycle, pulse width, pulse shape, etc. The modulation unit 502 may be surgically implanted, such as in a subcutaneous pocket of the abdomen or positioned outside the patient. By way of example, the modulation unit 502 may be purchased commercially, such as the Itrel 3 Model 7425 available from Medtronic, Inc. The modulation unit 502 is preferably programmed with a physician programmer, such as a Model 7432 also available from Medtronic, Inc.

The electrical leads and electrodes 500 are preferably selected to achieve respective impedances permitting a peak pulse current in the range from about 0.01 mA to about 100.0 mA.

The modulation signal may have a frequency selected to influence the therapeutic result, such as from about 0.2 pulses per minute to about 18,000 pulses per minute, depending on the application. The modulation signal may have a pulse width selected to influence the therapeutic result, such as from about 0.01 ms to 500.0 ms. The modulation signal may have a peak current amplitude selected to influence the therapeutic result, such as from about 0.01 mA to 100.0 mA.

In addition, or as an alternative to, the devices to implement the modulation unit 502 for producing the electrical voltage/current profile of the modulation signal to the electrodes 500, the device disclosed in U.S. patent Publication No.: 2005/0216062, may be employed, which was discussed in detail above.

As discussed above, the therapeutic treatment may also additionally or alternatively include using a pharmaceutical drug or drugs to modulate the nerves and/or muscles. This may be accomplished by means of an implantable pump and a catheter to administer the drug(s). The catheter preferably includes a discharge portion that lies adjacent a predetermined infusion site, e.g., one or more of the sites discussed above (or below) in the treatment. The modulation unit 502 is preferably operable to communicate with the pump to administer the drug(s) at predetermined dosage(s) in order to treat the disorder.

Treatment Approach 3

In accordance with one or more further embodiments of the present invention, a method of treating bronchial constriction includes inducing an electric field and/or electromagnetic field in the lungs of a mammal to reduce the over-growth of mucus, fibers, clogging, etc. of the lungs. For example, the electric field and/or electromagnetic field may be induced to down-regulate one or more mitogenic factors, such as vascular endothelial growth factor (VEGF), and/or one or more enzymes, such as matrix metalloproteinases (MMPs).

In the context of down-regulating VEGF, it is has been discovered that when VEGF is expressed in the lungs of genetically engineered transgenic mice, asthma-like alterations develop. Indeed, the presence (and over expression) of VEGF in mice produced many features of asthma, such as mucous formation, airway fibrosis and asthma-like pulmonary function abnormalities. It has also been previously discovered that if VEGF is blocked, the asthma-like manifestations in mouse asthma models is likewise blocked.

VEGF is a mitogenic factor that stimulates angiogenesis. Angiogenesis is the process of blood vessel growth (new capillary blood vessels as outgrowths of pre-existing vessels) towards a tissue in need of oxygen or an injured tissue. Angiogenesis can be either harmful or beneficial, for example, in cases such as tumor growth, angiogenesis towards the tumor can supply the tumor with nutrients and support its growth, thus further harming the patient.

At the onset of angiogenesis, the quiescent endothelium is destabilized into migratory, proliferative endothelial cells. The angiogenic (activated) endothelium is maintained primarily by positive regulatory molecules. In the absence of such molecules, the endothelium remains in a differentiated, quiescent state that is maintained by negative regulatory molecules, angiogenesis inhibitors. Normally, the negative and positive activities are balanced to maintain the vascular endothelium in quiescence. A shift in the balance of the positive and negative regulatory molecules can alter the differentiated state of the endothelium from the non-angiogenic, quiescent to the angiogenic state. In the switch to pro-angiogenesis, the quiescent endothelial cells are stimulated to migrate toward a chemotactic stimulus, lining up in a tube (sprout) formation. These cells also secrete proteolytic enzymes that degrade the endothelial basement membrane, thus allowing the migrating endothelial cells to extend into the perivascular stroma to begin a new capillary sprout. The angiogenic process is characterized by increased proliferation of endothelial cells to form the extending capillary.

In accordance with one or more aspects of the present invention, the mitogenic nature of the VEGF factor is believed to be the cause of the bronchial constrictions associated with, for example, asthma, and the resultant over-growth of mucus, fibers, clogging, etc. of the lungs. Thus, down-regulating the VEGF factor in treating the pathology is desirable.

There are naturally occurring molecules that serve as negative regulators of angiogenesis, such as angiostatin, a 38-45 kDa) cleavage product of plasminogen, containing kringle domains 1-4 (K1-4). Various attempts to block VEGF activity using non-natural means have also been proposed. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling. Monoclonal antibodies against VEGF have been shown to inhibit human tumor xenograft growth and ascites formation in mice. U.S. Pat. No. 6,342,221 to Thorpe, et al. discloses the use of anti-VEGF antibodies to specifically inhibit VEGF binding to the VEGFR-2 receptor.

The induction of electric field and/or electromagnetic field in the lungs to down-regulate VEGF, however, is an entirely different approach to treating bronchial constrictions (e.g., asthma). In accordance with one or more embodiments of the invention, the electric field and/or electromagnetic field may be induced by way of externally disposed apparatus, such as a control unit (including a drive signal generator) and percutaneous field emitters, such as capacitive coupling electrodes and/or inductive coils. (Alternative embodiments of the present invention may provide for subcutaneous components, including the control unit, signal generator, and/or the electrodes/coils).

The field emitters (whether disposed percutaneously or subcutaneously) are preferably located to direct the electric and/or electromagnetic fields toward the lungs of the patient. By way of example, the field emitters may be disposed on the chest of the patient and/or on the back of the patient. Particular locations for the field emitters are considered well within the knowledge and/or skill of artisans in the field.

The fields are induced by applying at least one electrical impulse the field emitters, such as by using the signal generator to apply the drive signals to the field emitters. By way of example, the drive signals may include at least one of sine waves, square waves, triangle waves, exponential waves, and complex impulses. In one or more embodiments, the signal generator may be implemented using a power source, a processor, a clock, a memory, etc. to produce the aforementioned waveforms, such as a pulse train. The parameters of the drive signal are preferably programmable, such as the frequency, amplitude, duty cycle, pulse width, pulse shape, etc. In the case of an implanted signal generator, programming may take place before or after implantation. For example, an implanted signal generator may have an external device for communication of settings to the generator. An external communication device may modify the signal generator programming to improve treatment.

By way of example, the parameters of the drive signal may include a sine wave profile having a frequency of between about 10 Hz to 100 KHz, a duty cycle of between about 1 to 100%, and an amplitude of between about 1 mv/cm to about 50 mv/cm. The electric fields and/or electromagnetic fields may be applied for a predetermined period of time, such as between about 0.5 to about 24 hours. The protocol of one or more embodiments of the present invention may include measuring a response of the patient to the applied field(s). For example, the airway pressure and/or lung volume of the patient may be monitored and the parameters of the drive signal (and thus the induced fields) may be adjusted to improve the treatment.

Studies have shown that people with allergies and asthma have an excess of T-helper type 2 cells (TH2); indeed, when VEGF is produced, the TH2 response is increased. (This condition has been mimicked in mice by over expressing VEGF in their lungs.) Thus, in accordance with one or more aspects of the present invention, the aforementioned application of electric fields and/or electromagnetic fields in the patient's lungs may be directed to the reduction of TH2 cells.

In one or more alternative embodiments, the application of electric fields and/or electromagnetic fields in the patient's lungs may be directed to the down-regulation of one or more enzymes, such as one or more matrix metalloproteinases (MMPs). MMPs are naturally-occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues. MMPs include one or more of: Stromelysin-1, gelatinase A, fibroblast collagenase (MMP-1), neutrophil collagenase (MMP-8), gelatinase B (MMP-9), stromelysin-2 (MMP-10), stromelysin-3 (MMP-11), matrilysin (MMP-7), collagenase 3 (MMP-13), and TNF-alpha converting enzyme (TACE).

The MMP enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma.

In accordance with one or more aspects of the present invention, however, the prevention and treatment of the aforementioned diseases associated with over-expression of MMPs (e.g., asthma) may be effected by inhibiting metalloproteinase enzymes using application of electric fields and/or electromagnetic fields in the patient's lungs. This, in turn is believed to curtail and/or eliminate the breakdown of connective tissues that results in the disease states.

Among the available devices to implement the control unit and/or signal generator for facilitating the emission of electric fields and/or electromagnetic fields is a physician programmer, such as a Model 7432 also available from Medtronic, Inc. An alternative control unit, signal generator is disclosed in U.S. patent Publication No.: 2005/0216062, the entire disclosure of which is incorporated herein by reference. U.S. patent Publication No.: 2005/0216062 discloses a multifunctional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or sawtooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating bronchial constriction associated with asthma or anaphylaxis comprising applying at least one electrical impulse to a selected region of a vagus nerve of a mammal in need of relief of bronchial smooth muscle constriction whereby a magnitude of constriction of the smooth muscle is reduced, wherein the electrical impulse has a frequency of 15 Hz to 35 Hz inclusive.

2. The method set forth in claim 1 wherein the selected region comprises an anterior pulmonary plexus.

3. The method set forth in claim 1 wherein the selected region comprises a posterior pulmonary plexus.

4. The method set forth in claim 1 wherein the selected region comprises a region of the vagus nerve proximal to a cardiac branch of the vagus nerve.

5. The method set forth in claim 1 wherein the selected region comprises a region of the vagus nerve proximal to a pulmonary branch of the vagus nerve.

6. A method of treating bronchial constriction associated with anaphylactic shock or asthma, comprising applying at least one electrical impulse to one or more selected regions of a vagus nerve of a mammal in need of relief of bronchial constriction, wherein the electrical impulse has a frequency of between 15 Hz to 35 Hz inclusive.

7. The method of claim 6, further comprising:
implanting one or more electrodes to the one or more selected regions of the vagus nerve; and
applying one or more electrical stimulation signals to the one or more electrodes to produce the at least one electrical impulse,
wherein the one or more electrical stimulation signals are of an amplitude of between 0.2 to 20 volts.

8. The method of claim 6, wherein the one or more electrical stimulation signals are of an amplitude of between 0.75 to 1.25 volts inclusive.

9. The method of claim 6, wherein the one or more electrical stimulation signals are one or more of a full or partial sinusoid, square wave, rectangular wave, triangle wave.

10. The method of claim 6, wherein the one or more electrical stimulation signals have a pulsed on-time of between 50 to 500 microseconds inclusive.

11. The method of claim 6, wherein the one or more electrical stimulation signals have a frequency of 25 Hz, and a pulsed on-time of 200-400 microseconds inclusive.

12. The method of claim 6, wherein the one or more electrical stimulation signals have a frequency of 25 Hz, and a pulsed on-time of between 100 to 400 microseconds inclusive.

13. The method of claim 12, wherein the pulsed on-time is one of: 400 microseconds, 200 microseconds, and 100 microseconds.

* * * * *